United States Patent
Stuyver et al.

(10) Patent No.: US 6,713,251 B2
(45) Date of Patent: *Mar. 30, 2004

(54) METHOD FOR DETECTION OF DRUG-INDUCED MUTATIONS IN THE REVERSE TRANSCRIPTASE GENE

(75) Inventors: Lieven Stuyver, Herzele (BE); Joost Louwagie, Zwijndrecht (BE); Rudi Rossau, Ekeren (BE)

(73) Assignee: Innogenetics N.V., Ghent (BE)

( * ) Notice: Subject to any disclaimer, the term of this patent is extended or adjusted under 35 U.S.C. 154(b) by 111 days.

This patent is subject to a terminal disclaimer.

(21) Appl. No.: 09/943,983

(22) Filed: Aug. 31, 2001

(65) Prior Publication Data

US 2003/0077575 A1 Apr. 24, 2003

Related U.S. Application Data

(62) Division of application No. 09/580,794, filed on May 30, 2000, now Pat. No. 6,331,389, which is a division of application No. 08/913,833, filed as application No. PCT/EP97/00211 on Jan. 17, 1997, now Pat. No. 6,087,093.

(30) Foreign Application Priority Data

Jan. 26, 1996 (EP) ............................. 96870005
Jun. 25, 1996 (EP) ............................. 96870081

(51) Int. Cl.$^7$ ........................... C12Q 1/70; C07H 21/04
(52) U.S. Cl. ..................... 435/5; 536/24.32; 536/24.33
(58) Field of Search ............................. 435/5, 6, 810; 536/24.3, 24.32, 24.33

(56) References Cited

U.S. PATENT DOCUMENTS

| | | | |
|---|---|---|---|
| 5,409,810 A | 4/1995 | Larder et al. | 435/5 |
| 5,534,424 A | * 7/1996 | Uhlen et al. | 435/91.2 |
| 5,631,128 A | 5/1997 | Kozal et al. | 435/5 |
| 5,759,770 A | 6/1998 | Guertler et al. | 435/5 |
| 5,827,648 A | 10/1998 | Eastman et al. | 435/5 |

FOREIGN PATENT DOCUMENTS

| | | | |
|---|---|---|---|
| EP | 0 422 762 A | 4/1991 | |
| EP | 0 532 258 A | 3/1993 | |
| WO | WO92/16180 A | 10/1992 | |
| WO | 93/21339 | * 10/1993 | C12Q/1/68 |
| WO | WO94/12670 A | 6/1994 | |

OTHER PUBLICATIONS

Mellors et al., "Mutations in HIV–1 Reverse Transcriptase and Protease Associated with Drug Resistance," *Int. Antiviral News* 3:8–13 (1995).

Schinazzi et al., "Mutations in HIV–1 Reverse Transcriptase and Protease Associated with Drug Resistance," *Int. Antiviral News* 2:72–74 (1994).

Larder et al., "Multiple Mutations in HIV–1 Reverse Transcriptase Confer High–Level Resistance to Zidovudine (AZT)," *Science* 246:1155–1158 (1989).

Eron et al., "Susceptibility Testing by Polymerase Chain Reaction DNA Quantitation: A Method to Measure Drug Resistance of Human Immunodeficiency Virus Type 1 Isolates," *Proceedings of the National Academy of Sciences of USA* 89:3241–3245 (1992).

Gingeras et al., "Use of Self–Sustained Sequence Replication Amplification Reaction to Analyze and Detect Mutations in Zidovudine–Resistant Human Immunodeficiency Virus," *The Journal of Infectious Diseases* 164:1066–1074 (1991).

Stuyver et al., "Typing of HCV Isolates and Characterisation of New Subtypes Using a Line Probe Assay," *J. Gen. Virol.* 74:1093–1102 (1993).

Lipshutz et al., "Using Oligonucleotide Probe Arrays to Access Genetic Diversity," *Biotechniques* 19:442–447 (1995).

Iversen et al., "Multidrug Resistant HIV –1 Strains Resulting from Combination Antiretroviral Therapy," *J. Virol.* 70:1086–1090 (1996).

Stuyver et al., "Line Probe Assay for Rapid Detection of Drug–Selected Mutations in the Human Immunodeficiency Virus Type 1 Reverse Transcriptase Gene," *Antimicrobial Agents and Chemotherapy* 41:284–291 (1997).

Shafer et al., "Drug resistance and heterogeneous long–term virologic responses of human immunodeficiency virus type 1–infected subjects to zidovudine and didanosine combination therapy", *J. Inf. Diseases*, 172:70–78 (1995).

* cited by examiner

*Primary Examiner*—Kenneth R. Horlick
(74) *Attorney, Agent, or Firm*—Howrey Simon Arnold & White, LLP

(57) ABSTRACT

The present invention relates to a method for the rapid and reliable detection of drug-induced mutations in the reverse transcriptase gene allowing the simultaneous characterization of a range of codons involved in drug resistance using specific sets of probes optimized to function together in a reverse-hybridization assay. More particularly, the present invention relates to a method for determining the susceptibility to antiviral drugs of HIV strains present in a biological sample, comprising: (i) if need be releasing, isolating or concentrating the polynucleic acids present in the sample; (ii) if need be amplifying the relevant part of the reverse transcriptase genes present in said sample with at least one suitable primer pair; (iii) hybridizing the polynucleic acids of step (i) or (ii) with at least two RT gene probes hybridizing specifically to one or more target sequences with said probes being applied to known locations on a solid support and with said probes being capable of simultaneously hybridizing to their respective target regions under appropriate hybridization and wash conditions allowing the detection of homologous targets, or said probes hybridizing specifically with a sequence complementary to any of said target sequences, or a sequence wherein T is replaced by U; (iv) detecting the hybrids formed in step (iii); (v) inferring the nucleotide sequence at the codons of interest and/or the amino acids of the codons of interest and/or antiviral drug resistance spectrum, and possibly the type of HIV isolates involved from the differential hybridization signal(s) obtained in step (iv).

23 Claims, 9 Drawing Sheets

FIG. 1A *Region I*

Figure 2A:
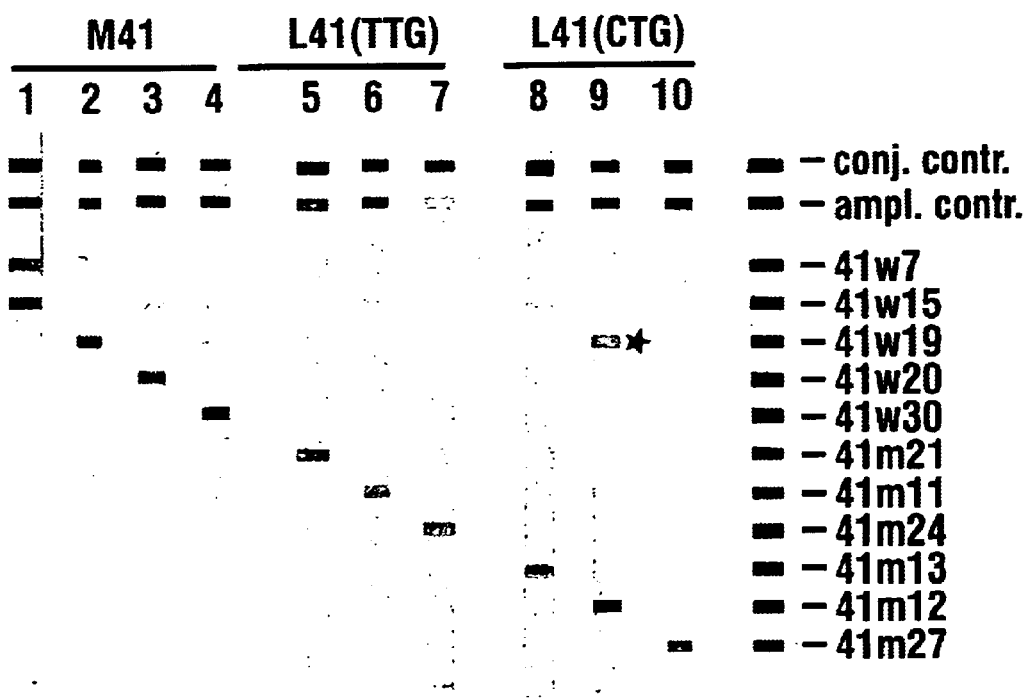
Figure 2B:
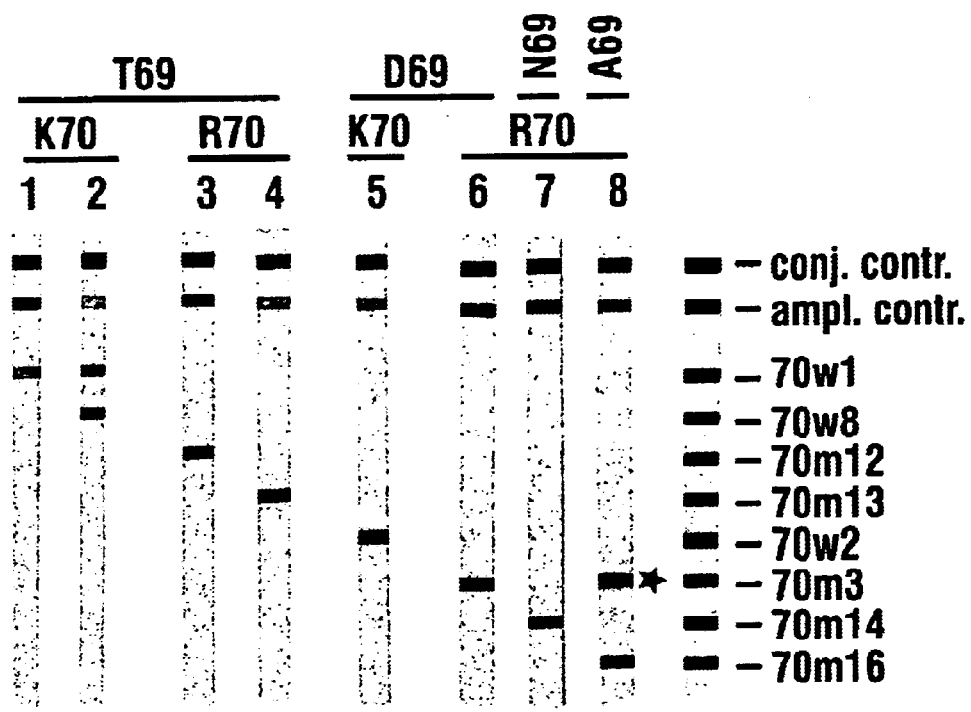
Figure 2C:
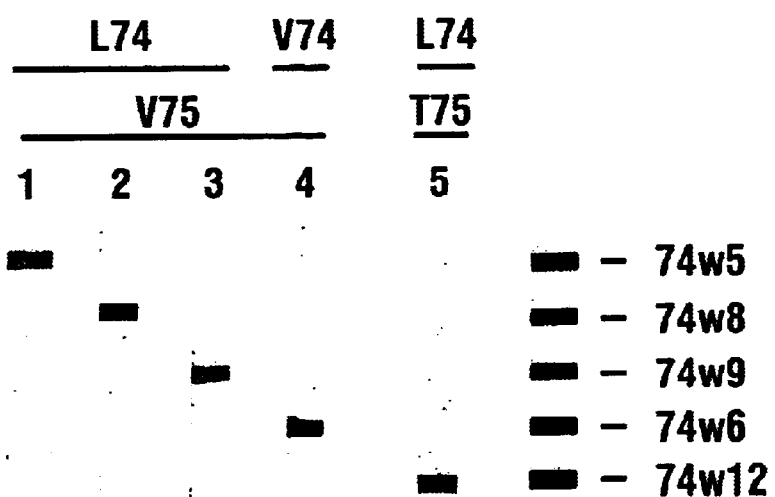
Figure 2D:
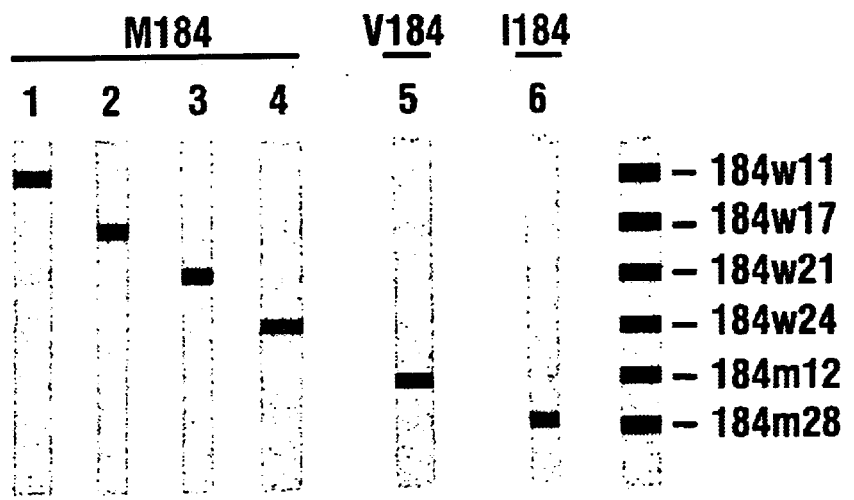
Figure 2E:
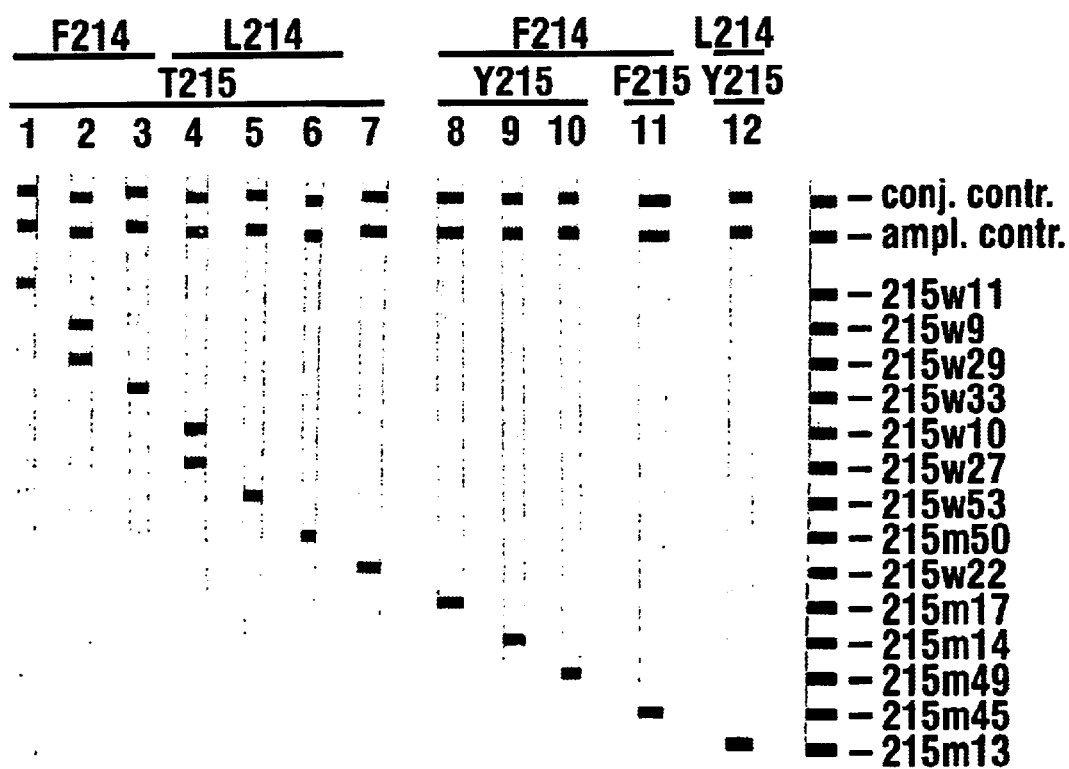

```
    38   39   40   41   42   43   44
    TGT  ACA  GAA  ATG  GAA  AAG  GAA
              G    T         G    A
                   C              G
```

FIG. 1B *Region II*

```
    47   48   49   50   51   52   53
    ATT  TCA  AAA  ATT  GGG  CCT  GAA
              G    G
                   C
                   C
```

FIG. 1C *Region III*

```
    65   66   67   68   69   70   71   72
    AAA  AAA  GAC  AGT  ACT  AAA  TGG  AGA
    G    G    A         A    G
                        A         G
                        GA
                        G
```

FIG. 1D *Region IV*

```
    73   74   75   76   77
    AAA  TTA  GTA  GAT  TTC
    G    G         G    C
              AC
```

FIG. 1E *Region V*

```
    148  149  150  151  152  153  154
    GTG  CTT  CCA  CAG  GGA  TGG  AAA
              C    AT
         G         G    A
                        T
```

FIG. 1F *Region VI*

```
    180  181  182  183  184  185  186  187
    ATC  TAT  CAA  TAC  ATG  GAT  GAT  TTA
              G    T    A    C    G    GG
                             G              G
         G                   G
```

FIG. 1G  *Region VII*

```
      212 213 214 215 216
      TGG GGA TTT ACC ACA
              G   C   T
              A   TA
              C   TT
```

FIG. 1H  *Region VIII*

```
      217 218 219 220
      CCA GAC AAA AAA
              T   G   G
                  C
                  G
```

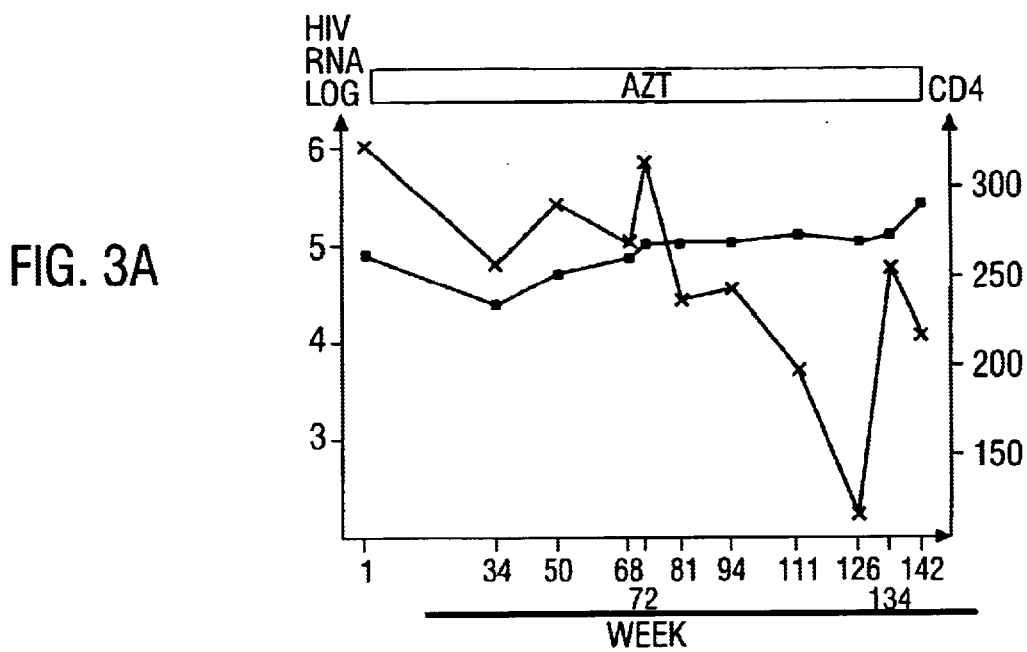
FIG. 3A
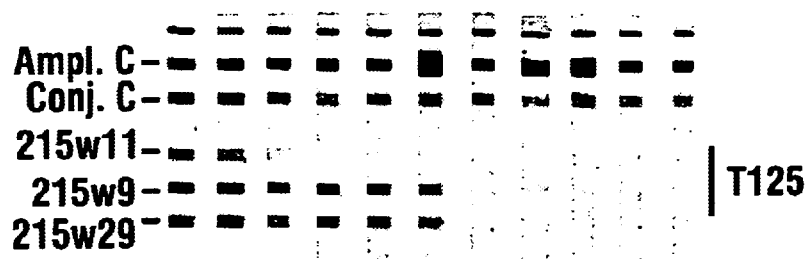
FIG. 3B
FIG. 3C
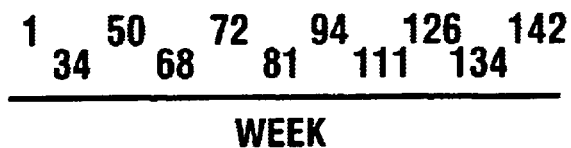

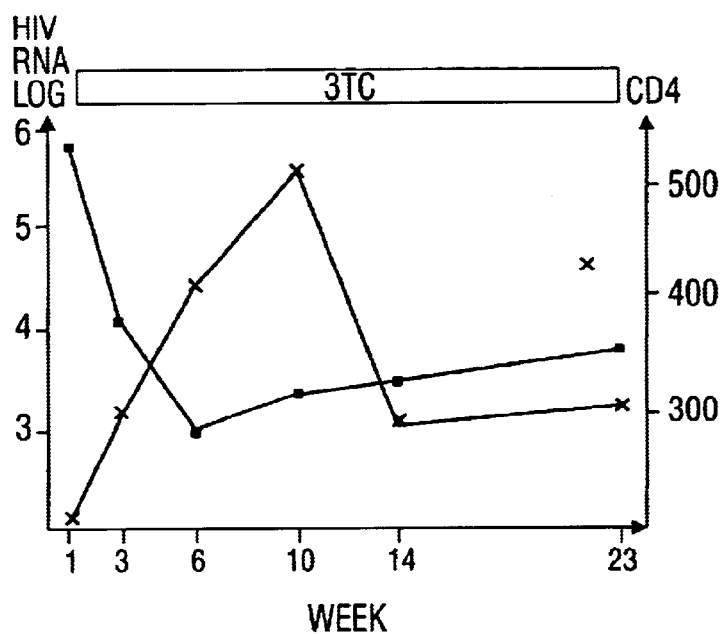
FIG. 3D
FIG. 3E
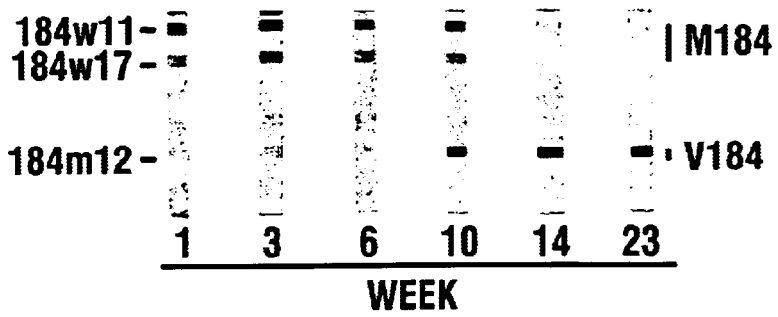
FIG. 3F

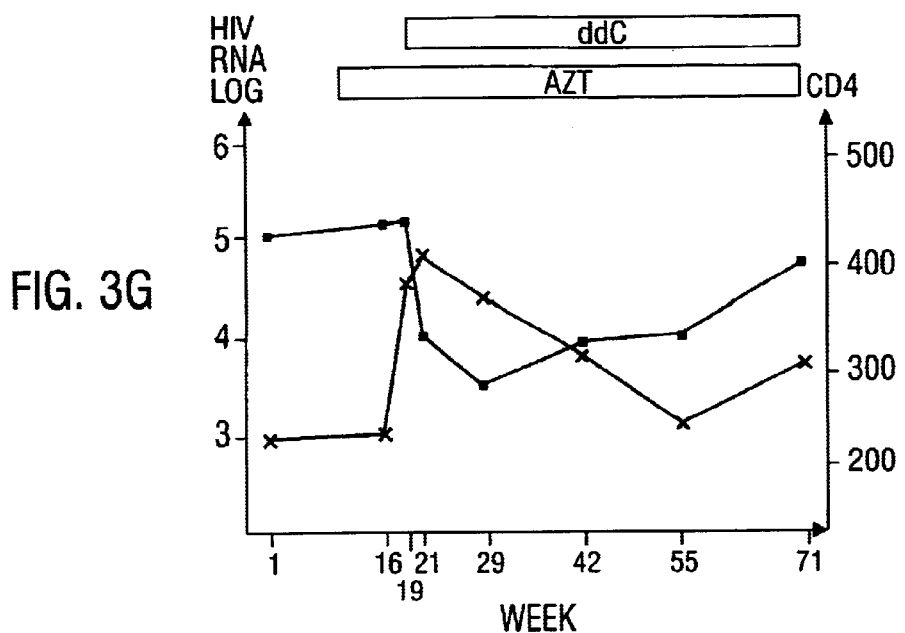
FIG. 3G
FIG. 3H
| 70: | K | K | K | K | K | K<br>R | R |
|---|---|---|---|---|---|---|---|
| 214: | F | F<br>L | F<br>L | L | L | R<br>F<br>L<br>T<br>Y | F |
| 215: | T | T | T | T | T | T<br>Y | Y |
| 219: | K | K | K | K | K | K | K<br>E |
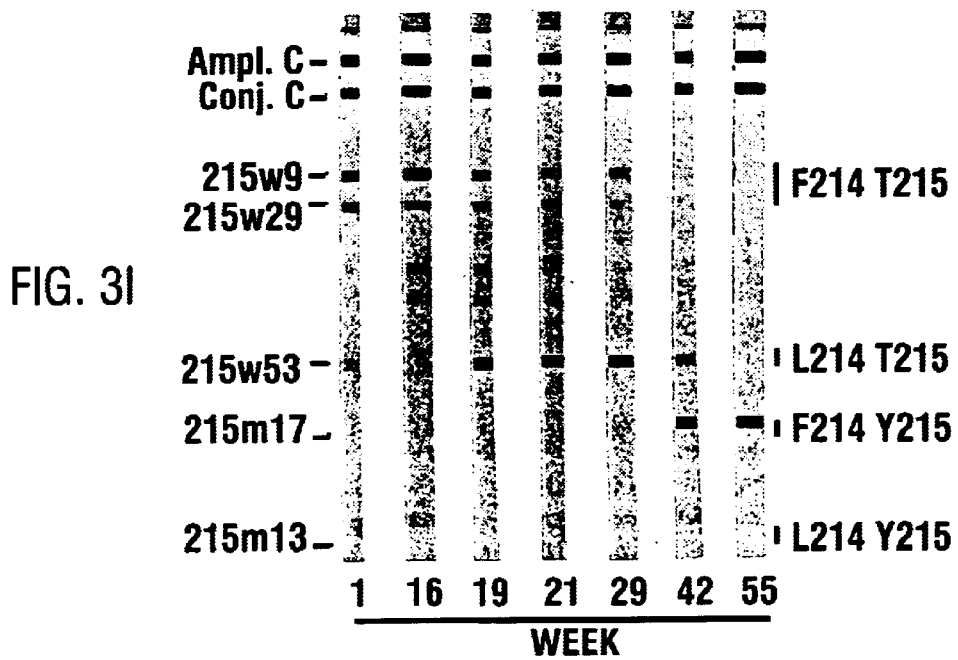
FIG. 3I

```
                        SEQUENCE LISTING

<160> NUMBER OF SEQ ID NOS: 164

<210> SEQ ID NO 1
<211> LENGTH: 15
<212> TYPE: DNA
<213> ORGANISM: Artificial sequence
<220> FEATURE:
<223> OTHER INFORMATION: Synthetic Primer

<400> SEQUENCE: 1
agaaatggaa aagga                                                  15

<210> SEQ ID NO 2
<211> LENGTH: 15
<212> TYPE: DNA
<213> ORGANISM: Artificial sequence
<220> FEATURE:
<223> OTHER INFORMATION: Synthetic Primer

<400> SEQUENCE: 2
tgtacagaaa tggaa                                                  15

<210> SEQ ID NO 3
<211> LENGTH: 15
<212> TYPE: DNA
<213> ORGANISM: Artificial sequence
<220> FEATURE:
<223> OTHER INFORMATION: Synthetic Primer

<400> SEQUENCE: 3
aaatggaaaa ggaag                                                  15

<210> SEQ ID NO 4
<211> LENGTH: 14
<212> TYPE: DNA
<213> ORGANISM: Artificial sequence
<220> FEATURE:
<223> OTHER INFORMATION: Synthetic Primer

<400> SEQUENCE: 4
tacagagatg gaaa                                                   14

<210> SEQ ID NO 5
<211> LENGTH: 15
<212> TYPE: DNA
<213> ORGANISM: Artificial sequence
<220> FEATURE:
<223> OTHER INFORMATION: Synthetic Primer

<400> SEQUENCE: 5
gtacagagat ggaaa                                                  15
```

```
<210> SEQ ID NO 6
<211> LENGTH: 15
<212> TYPE: DNA
<213> ORGANISM: Artificial sequence
<220> FEATURE:
<223> OTHER INFORMATION: Synthetic Primer

<400> SEQUENCE: 6
agagatggaa aaaga                                                          15

<210> SEQ ID NO 7
<211> LENGTH: 15
<212> TYPE: DNA
<213> ORGANISM: Artificial sequence
<220> FEATURE:
<223> OTHER INFORMATION: Synthetic Primer

<400> SEQUENCE: 7
agaaatggag aagga                                                          15

<210> SEQ ID NO 8
<211> LENGTH: 14
<212> TYPE: DNA
<213> ORGANISM: Artificial sequence
<220> FEATURE:
<223> OTHER INFORMATION: Synthetic Primer

<400> SEQUENCE: 8
acagagatgg aaaa                                                           14

<210> SEQ ID NO 9
<211> LENGTH: 14
<212> TYPE: DNA
<213> ORGANISM: Artificial sequence
<220> FEATURE:
<223> OTHER INFORMATION: Synthetic Primer

<400> SEQUENCE: 9
gtacagagat ggaa                                                           14

<210> SEQ ID NO 10
<211> LENGTH: 14
<212> TYPE: DNA
<213> ORGANISM: Artificial sequence
<220> FEATURE:
<223> OTHER INFORMATION: Synthetic Primer

<400> SEQUENCE: 10
cagagatgga aaag                                                           14

<210> SEQ ID NO 11
<211> LENGTH: 15
<212> TYPE: DNA
<213> ORGANISM: Artificial sequence
<220> FEATURE:
<223> OTHER INFORMATION: Synthetic Primer

<400> SEQUENCE: 11
agaaatggaa aaaga                                                          15

<210> SEQ ID NO 12
<211> LENGTH: 14
<212> TYPE: DNA
<213> ORGANISM: Artificial sequence
<220> FEATURE:
<223> OTHER INFORMATION: Synthetic Primer
```

-continued

<400> SEQUENCE: 12
gaaatggaaa aaga                                                                14

<210> SEQ ID NO 13
<211> LENGTH: 16
<212> TYPE: DNA
<213> ORGANISM: Artificial sequence
<220> FEATURE:
<223> OTHER INFORMATION: Synthetic Primer

<400> SEQUENCE: 13
cagaaatgga aaaaga                                                              16

<210> SEQ ID NO 14
<211> LENGTH: 16
<212> TYPE: DNA
<213> ORGANISM: Artificial sequence
<220> FEATURE:
<223> OTHER INFORMATION: Synthetic Primer

<400> SEQUENCE: 14
agaaatggaa aaagaa                                                              16

<210> SEQ ID NO 15
<211> LENGTH: 15
<212> TYPE: DNA
<213> ORGANISM: Artificial sequence
<220> FEATURE:
<223> OTHER INFORMATION: Synthetic Primer

<400> SEQUENCE: 15
agaattggaa aagga                                                               15

<210> SEQ ID NO 16
<211> LENGTH: 15
<212> TYPE: DNA
<213> ORGANISM: Artificial sequence
<220> FEATURE:
<223> OTHER INFORMATION: Synthetic Primer

<400> SEQUENCE: 16
agagttggaa aagga                                                               15

<210> SEQ ID NO 17
<211> LENGTH: 14
<212> TYPE: DNA
<213> ORGANISM: Artificial sequence
<220> FEATURE:
<223> OTHER INFORMATION: Synthetic Primer

<400> SEQUENCE: 17
agagctggaa aagg                                                                14

<210> SEQ ID NO 18
<211> LENGTH: 14
<212> TYPE: DNA
<213> ORGANISM: Artificial sequence
<220> FEATURE:
<223> OTHER INFORMATION: Synthetic Primer

<400> SEQUENCE: 18
agaactggaa aagg                                                                14

<210> SEQ ID NO 19
<211> LENGTH: 13

```
<212> TYPE: DNA
<213> ORGANISM: Artificial sequence
<220> FEATURE:
<223> OTHER INFORMATION: Synthetic Primer

<400> SEQUENCE: 19
gagctggaaa agg                                                    13

<210> SEQ ID NO 20
<211> LENGTH: 15
<212> TYPE: DNA
<213> ORGANISM: Artificial sequence
<220> FEATURE:
<223> OTHER INFORMATION: Synthetic Primer

<400> SEQUENCE: 20
acagaattgg aaaag                                                  15

<210> SEQ ID NO 21
<211> LENGTH: 14
<212> TYPE: DNA
<213> ORGANISM: Artificial sequence
<220> FEATURE:
<223> OTHER INFORMATION: Synthetic Primer

<400> SEQUENCE: 21
acagaattgg aaaa                                                   14

<210> SEQ ID NO 22
<211> LENGTH: 14
<212> TYPE: DNA
<213> ORGANISM: Artificial sequence
<220> FEATURE:
<223> OTHER INFORMATION: Synthetic Primer

<400> SEQUENCE: 22
acagaactgg aaaa                                                   14

<210> SEQ ID NO 23
<211> LENGTH: 14
<212> TYPE: DNA
<213> ORGANISM: Artificial sequence
<220> FEATURE:
<223> OTHER INFORMATION: Synthetic Primer

<400> SEQUENCE: 23
agaattggaa gagg                                                   14

<210> SEQ ID NO 24
<211> LENGTH: 15
<212> TYPE: DNA
<213> ORGANISM: Artificial sequence
<220> FEATURE:
<223> OTHER INFORMATION: Synthetic Primer

<400> SEQUENCE: 24
cagaattgga agagg                                                  15

<210> SEQ ID NO 25
<211> LENGTH: 15
<212> TYPE: DNA
<213> ORGANISM: Artificial sequence
<220> FEATURE:
<223> OTHER INFORMATION: Synthetic Primer

<400> SEQUENCE: 25
```

```
agaattggaa gagga                                                    15

<210> SEQ ID NO 26
<211> LENGTH: 14
<212> TYPE: DNA
<213> ORGANISM: Artificial sequence
<220> FEATURE:
<223> OTHER INFORMATION: Synthetic Primer

<400> SEQUENCE: 26
agaactggaa gagg                                                     14

<210> SEQ ID NO 27
<211> LENGTH: 15
<212> TYPE: DNA
<213> ORGANISM: Artificial sequence
<220> FEATURE:
<223> OTHER INFORMATION: Synthetic Primer

<400> SEQUENCE: 27
cagaactgga agagg                                                    15

<210> SEQ ID NO 28
<211> LENGTH: 15
<212> TYPE: DNA
<213> ORGANISM: Artificial sequence
<220> FEATURE:
<223> OTHER INFORMATION: Synthetic Primer

<400> SEQUENCE: 28
agaactggaa gagga                                                    15

<210> SEQ ID NO 29
<211> LENGTH: 14
<212> TYPE: DNA
<213> ORGANISM: Artificial sequence
<220> FEATURE:
<223> OTHER INFORMATION: Synthetic Primer

<400> SEQUENCE: 29
caaaaattgg gcct                                                     14

<210> SEQ ID NO 30
<211> LENGTH: 15
<212> TYPE: DNA
<213> ORGANISM: Artificial sequence
<220> FEATURE:
<223> OTHER INFORMATION: Synthetic Primer

<400> SEQUENCE: 30
atttcaagaa ttggg                                                    15

<210> SEQ ID NO 31
<211> LENGTH: 14
<212> TYPE: DNA
<213> ORGANISM: Artificial sequence
<220> FEATURE:
<223> OTHER INFORMATION: Synthetic Primer

<400> SEQUENCE: 31
ttcaaaagtt gggc                                                     14

<210> SEQ ID NO 32
<211> LENGTH: 15
<212> TYPE: DNA
<213> ORGANISM: Artificial sequence
```

```
<220> FEATURE:
<223> OTHER INFORMATION: Synthetic Primer

<400> SEQUENCE: 32
caaaaatcgg gcctg                                                    15

<210> SEQ ID NO 33
<211> LENGTH: 15
<212> TYPE: DNA
<213> ORGANISM: Artificial sequence
<220> FEATURE:
<223> OTHER INFORMATION: Synthetic Primer

<400> SEQUENCE: 33
aaaaatcggg cctga                                                    15

<210> SEQ ID NO 34
<211> LENGTH: 15
<212> TYPE: DNA
<213> ORGANISM: Artificial sequence
<220> FEATURE:
<223> OTHER INFORMATION: Synthetic Primer

<400> SEQUENCE: 34
aaagaagaaa gacag                                                    15

<210> SEQ ID NO 35
<211> LENGTH: 19
<212> TYPE: DNA
<213> ORGANISM: Artificial sequence
<220> FEATURE:
<223> OTHER INFORMATION: Synthetic Primer

<400> SEQUENCE: 35
ataaagaaaa agaacagta                                                19

<210> SEQ ID NO 36
<211> LENGTH: 16
<212> TYPE: DNA
<213> ORGANISM: Artificial sequence
<220> FEATURE:
<223> OTHER INFORMATION: Synthetic Primer

<400> SEQUENCE: 36
agtactaaat ggagaa                                                   16

<210> SEQ ID NO 37
<211> LENGTH: 16
<212> TYPE: DNA
<213> ORGANISM: Artificial sequence
<220> FEATURE:
<223> OTHER INFORMATION: Synthetic Primer

<400> SEQUENCE: 37
agtgataaat ggagaa                                                   16

<210> SEQ ID NO 38
<211> LENGTH: 16
<212> TYPE: DNA
<213> ORGANISM: Artificial sequence
<220> FEATURE:
<223> OTHER INFORMATION: Synthetic Primer

<400> SEQUENCE: 38
acagtactaa atggag                                                   16
```

<210> SEQ ID NO 39
<211> LENGTH: 27
<212> TYPE: DNA
<213> ORGANISM: Artificial sequence
<220> FEATURE:
<223> OTHER INFORMATION: Synthetic Primer

<400> SEQUENCE: 39
atcaggatgg agttcataac ccatcca                              27

<210> SEQ ID NO 40
<211> LENGTH: 16
<212> TYPE: DNA
<213> ORGANISM: Artificial sequence
<220> FEATURE:
<223> OTHER INFORMATION: Synthetic Primer

<400> SEQUENCE: 40
taaatggaga aaatag                                          16

<210> SEQ ID NO 41
<211> LENGTH: 15
<212> TYPE: DNA
<213> ORGANISM: Artificial sequence
<220> FEATURE:
<223> OTHER INFORMATION: Synthetic Primer

<400> SEQUENCE: 41
gtgatagatg gagaa                                           15

<210> SEQ ID NO 42
<211> LENGTH: 14
<212> TYPE: DNA
<213> ORGANISM: Artificial sequence
<220> FEATURE:
<223> OTHER INFORMATION: Synthetic Primer

<400> SEQUENCE: 42
gtactagatg gaga                                            14

<210> SEQ ID NO 43
<211> LENGTH: 15
<212> TYPE: DNA
<213> ORGANISM: Artificial sequence
<220> FEATURE:
<223> OTHER INFORMATION: Synthetic Primer

<400> SEQUENCE: 43
agtactagat ggaga                                           15

<210> SEQ ID NO 44
<211> LENGTH: 15
<212> TYPE: DNA
<213> ORGANISM: Artificial sequence
<220> FEATURE:
<223> OTHER INFORMATION: Synthetic Primer

<400> SEQUENCE: 44
cagtaataga tggag                                           15

<210> SEQ ID NO 45
<211> LENGTH: 15
<212> TYPE: DNA
<213> ORGANISM: Artificial sequence
<220> FEATURE:
<223> OTHER INFORMATION: Synthetic Primer

```
<400> SEQUENCE: 45
cagtaataga tggag                                              15

<210> SEQ ID NO 46
<211> LENGTH: 15
<212> TYPE: DNA
<213> ORGANISM: Artificial sequence
<220> FEATURE:
<223> OTHER INFORMATION: Synthetic Primer

<400> SEQUENCE: 46
acagtgctag atgga                                              15

<210> SEQ ID NO 47
<211> LENGTH: 14
<212> TYPE: DNA
<213> ORGANISM: Artificial sequence
<220> FEATURE:
<223> OTHER INFORMATION: Synthetic Primer

<400> SEQUENCE: 47
cagtgctaga tgga                                               14

<210> SEQ ID NO 48
<211> LENGTH: 14
<212> TYPE: DNA
<213> ORGANISM: Artificial sequence
<220> FEATURE:
<223> OTHER INFORMATION: Synthetic Primer

<400> SEQUENCE: 48
cagtgctaga tgga                                               14

<210> SEQ ID NO 49
<211> LENGTH: 14
<212> TYPE: DNA
<213> ORGANISM: Artificial sequence
<220> FEATURE:
<223> OTHER INFORMATION: Synthetic Primer

<400> SEQUENCE: 49
cagtgataga tgga                                               14

<210> SEQ ID NO 50
<211> LENGTH: 15
<212> TYPE: DNA
<213> ORGANISM: Artificial sequence
<220> FEATURE:
<223> OTHER INFORMATION: Synthetic Primer

<400> SEQUENCE: 50
cagtgataga tggag                                              15

<210> SEQ ID NO 51
<211> LENGTH: 14
<212> TYPE: DNA
<213> ORGANISM: Artificial sequence
<220> FEATURE:
<223> OTHER INFORMATION: Synthetic Primer

<400> SEQUENCE: 51
agtgatagat ggag                                               14

<210> SEQ ID NO 52
```

-continued

<211> LENGTH: 15
<212> TYPE: DNA
<213> ORGANISM: Artificial sequence
<220> FEATURE:
<223> OTHER INFORMATION: Synthetic Primer

<400> SEQUENCE: 52
agtgatagat ggaga                                               15

<210> SEQ ID NO 53
<211> LENGTH: 18
<212> TYPE: DNA
<213> ORGANISM: Artificial sequence
<220> FEATURE:
<223> OTHER INFORMATION: Synthetic Primer

<400> SEQUENCE: 53
gagaaaatta gtagattt                                            18

<210> SEQ ID NO 54
<211> LENGTH: 16
<212> TYPE: DNA
<213> ORGANISM: Artificial sequence
<220> FEATURE:
<223> OTHER INFORMATION: Synthetic Primer

<400> SEQUENCE: 54
aaaattagta gacttc                                              16

<210> SEQ ID NO 55
<211> LENGTH: 17
<212> TYPE: DNA
<213> ORGANISM: Artificial sequence
<220> FEATURE:
<223> OTHER INFORMATION: Synthetic Primer

<400> SEQUENCE: 55
gagaaagtta gtggatt                                             17

<210> SEQ ID NO 56
<211> LENGTH: 17
<212> TYPE: DNA
<213> ORGANISM: Artificial sequence
<220> FEATURE:
<223> OTHER INFORMATION: Synthetic Primer

<400> SEQUENCE: 56
agaaaagtag tagattt                                             17

<210> SEQ ID NO 57
<211> LENGTH: 16
<212> TYPE: DNA
<213> ORGANISM: Artificial sequence
<220> FEATURE:
<223> OTHER INFORMATION: Synthetic Primer

<400> SEQUENCE: 57
aaaattaaca gatttc                                              16

<210> SEQ ID NO 58
<211> LENGTH: 16
<212> TYPE: DNA
<213> ORGANISM: Artificial sequence
<220> FEATURE:
<223> OTHER INFORMATION: Synthetic Primer

<400> SEQUENCE: 58

-continued gaaaattaac agattt                                                16

<210> SEQ ID NO 59
<211> LENGTH: 17
<212> TYPE: DNA
<213> ORGANISM: Artificial sequence
<220> FEATURE:
<223> OTHER INFORMATION: Synthetic Primer

<400> SEQUENCE: 59
gaaaattaac agatttc                                               17

<210> SEQ ID NO 60
<211> LENGTH: 15
<212> TYPE: DNA
<213> ORGANISM: Artificial sequence
<220> FEATURE:
<223> OTHER INFORMATION: Synthetic Primer

<400> SEQUENCE: 60
cttccacagg gatgg                                                 15

<210> SEQ ID NO 61
<211> LENGTH: 15
<212> TYPE: DNA
<213> ORGANISM: Artificial sequence
<220> FEATURE:
<223> OTHER INFORMATION: Synthetic Primer

<400> SEQUENCE: 61
cttccacaag gatgg                                                 15

<210> SEQ ID NO 62
<211> LENGTH: 16
<212> TYPE: DNA
<213> ORGANISM: Artificial sequence
<220> FEATURE:
<223> OTHER INFORMATION: Synthetic Primer

<400> SEQUENCE: 62
tgctcccaca gggatg                                                16

<210> SEQ ID NO 63
<211> LENGTH: 15
<212> TYPE: DNA
<213> ORGANISM: Artificial sequence
<220> FEATURE:
<223> OTHER INFORMATION: Synthetic Primer

<400> SEQUENCE: 63
cttccaatgg gatgg                                                 15

<210> SEQ ID NO 64
<211> LENGTH: 16
<212> TYPE: DNA
<213> ORGANISM: Artificial sequence
<220> FEATURE:
<223> OTHER INFORMATION: Synthetic Primer

<400> SEQUENCE: 64
gcttccaatg ggatgg                                                16

<210> SEQ ID NO 65
<211> LENGTH: 18
<212> TYPE: DNA

```
<213> ORGANISM: Artificial sequence
<220> FEATURE:
<223> OTHER INFORMATION: Synthetic Primer

<400> SEQUENCE: 65
agttatctat caatacag                                         18

<210> SEQ ID NO 66
<211> LENGTH: 16
<212> TYPE: DNA
<213> ORGANISM: Artificial sequence
<220> FEATURE:
<223> OTHER INFORMATION: Synthetic Primer

<400> SEQUENCE: 66
agttatctgt caatac                                           16

<210> SEQ ID NO 67
<211> LENGTH: 17
<212> TYPE: DNA
<213> ORGANISM: Artificial sequence
<220> FEATURE:
<223> OTHER INFORMATION: Synthetic Primer

<400> SEQUENCE: 67
tcaatacatg gatgagg                                          17

<210> SEQ ID NO 68
<211> LENGTH: 17
<212> TYPE: DNA
<213> ORGANISM: Artificial sequence
<220> FEATURE:
<223> OTHER INFORMATION: Synthetic Primer

<400> SEQUENCE: 68
tcagtacatg gatgagg                                          17

<210> SEQ ID NO 69
<211> LENGTH: 16
<212> TYPE: DNA
<213> ORGANISM: Artificial sequence
<220> FEATURE:
<223> OTHER INFORMATION: Synthetic Primer

<400> SEQUENCE: 69
atcaatacat ggatga                                           16

<210> SEQ ID NO 70
<211> LENGTH: 14
<212> TYPE: DNA
<213> ORGANISM: Artificial sequence
<220> FEATURE:
<223> OTHER INFORMATION: Synthetic Primer

<400> SEQUENCE: 70
tcagtacatg gatg                                             14

<210> SEQ ID NO 71
<211> LENGTH: 15
<212> TYPE: DNA
<213> ORGANISM: Artificial sequence
<220> FEATURE:
<223> OTHER INFORMATION: Synthetic Primer

<400> SEQUENCE: 71
atcaatatat ggatg                                            15
```

-continued

<210> SEQ ID NO 72
<211> LENGTH: 16
<212> TYPE: DNA
<213> ORGANISM: Artificial sequence
<220> FEATURE:
<223> OTHER INFORMATION: Synthetic Primer

<400> SEQUENCE: 72
atcaatatat ggatga                                                    16

<210> SEQ ID NO 73
<211> LENGTH: 15
<212> TYPE: DNA
<213> ORGANISM: Artificial sequence
<220> FEATURE:
<223> OTHER INFORMATION: Synthetic Primer

<400> SEQUENCE: 73
tcaatatatg gatga                                                     15

<210> SEQ ID NO 74
<211> LENGTH: 15
<212> TYPE: DNA
<213> ORGANISM: Artificial sequence
<220> FEATURE:
<223> OTHER INFORMATION: Synthetic Primer

<400> SEQUENCE: 74
tcaatacatg gacga                                                     15

<210> SEQ ID NO 75
<211> LENGTH: 15
<212> TYPE: DNA
<213> ORGANISM: Artificial sequence
<220> FEATURE:
<223> OTHER INFORMATION: Synthetic Primer

<400> SEQUENCE: 75
caatacatgg acgat                                                     15

<210> SEQ ID NO 76
<211> LENGTH: 16
<212> TYPE: DNA
<213> ORGANISM: Artificial sequence
<220> FEATURE:
<223> OTHER INFORMATION: Synthetic Primer

<400> SEQUENCE: 76
tcaatacatg gacgat                                                    16

<210> SEQ ID NO 77
<211> LENGTH: 17
<212> TYPE: DNA
<213> ORGANISM: Artificial sequence
<220> FEATURE:
<223> OTHER INFORMATION: Synthetic Primer

<400> SEQUENCE: 77
caatacgtgg atgaggg                                                   17

<210> SEQ ID NO 78
<211> LENGTH: 14
<212> TYPE: DNA
<213> ORGANISM: Artificial sequence
<220> FEATURE:

-continued

<223> OTHER INFORMATION: Synthetic Primer

<400> SEQUENCE: 78
aatacataga tgat    14

<210> SEQ ID NO 79
<211> LENGTH: 15
<212> TYPE: DNA
<213> ORGANISM: Artificial sequence
<220> FEATURE:
<223> OTHER INFORMATION: Synthetic Primer

<400> SEQUENCE: 79
caatacatag atgat    15

<210> SEQ ID NO 80
<211> LENGTH: 16
<212> TYPE: DNA
<213> ORGANISM: Artificial sequence
<220> FEATURE:
<223> OTHER INFORMATION: Synthetic Primer

<400> SEQUENCE: 80
caatacatag atgatt    16

<210> SEQ ID NO 81
<211> LENGTH: 15
<212> TYPE: DNA
<213> ORGANISM: Artificial sequence
<220> FEATURE:
<223> OTHER INFORMATION: Synthetic Primer

<400> SEQUENCE: 81
caatacgtag atgat    15

<210> SEQ ID NO 82
<211> LENGTH: 15
<212> TYPE: DNA
<213> ORGANISM: Artificial sequence
<220> FEATURE:
<223> OTHER INFORMATION: Synthetic Primer

<400> SEQUENCE: 82
tcaatacgtg gatga    15

<210> SEQ ID NO 83
<211> LENGTH: 16
<212> TYPE: DNA
<213> ORGANISM: Artificial sequence
<220> FEATURE:
<223> OTHER INFORMATION: Synthetic Primer

<400> SEQUENCE: 83
tcaatacata gatgat    16

<210> SEQ ID NO 84
<211> LENGTH: 17
<212> TYPE: DNA
<213> ORGANISM: Artificial sequence
<220> FEATURE:
<223> OTHER INFORMATION: Synthetic Primer

<400> SEQUENCE: 84
atcaatacat agatgat    17

```
<210> SEQ ID NO 85
<211> LENGTH: 15
<212> TYPE: DNA
<213> ORGANISM: Artificial sequence
<220> FEATURE:
<223> OTHER INFORMATION: Synthetic Primer

<400> SEQUENCE: 85
ggatttacca cacca                                                    15

<210> SEQ ID NO 86
<211> LENGTH: 14
<212> TYPE: DNA
<213> ORGANISM: Artificial sequence
<220> FEATURE:
<223> OTHER INFORMATION: Synthetic Primer

<400> SEQUENCE: 86
gacttaccac acca                                                     14

<210> SEQ ID NO 87
<211> LENGTH: 14
<212> TYPE: DNA
<213> ORGANISM: Artificial sequence
<220> FEATURE:
<223> OTHER INFORMATION: Synthetic Primer

<400> SEQUENCE: 87
ggtttaccac acca                                                     14

<210> SEQ ID NO 88
<211> LENGTH: 14
<212> TYPE: DNA
<213> ORGANISM: Artificial sequence
<220> FEATURE:
<223> OTHER INFORMATION: Synthetic Primer

<400> SEQUENCE: 88
gatttaccac acca                                                     14

<210> SEQ ID NO 89
<211> LENGTH: 14
<212> TYPE: DNA
<213> ORGANISM: Artificial sequence
<220> FEATURE:
<223> OTHER INFORMATION: Synthetic Primer

<400> SEQUENCE: 89
ttactacacc agac                                                     14

<210> SEQ ID NO 90
<211> LENGTH: 13
<212> TYPE: DNA
<213> ORGANISM: Artificial sequence
<220> FEATURE:
<223> OTHER INFORMATION: Synthetic Primer

<400> SEQUENCE: 90
ttaccacacc aga                                                      13

<210> SEQ ID NO 91
<211> LENGTH: 14
<212> TYPE: DNA
<213> ORGANISM: Artificial sequence
<220> FEATURE:
<223> OTHER INFORMATION: Synthetic Primer
```

```
<400> SEQUENCE: 91
tggggactta ccac                                                    14

<210> SEQ ID NO 92
<211> LENGTH: 14
<212> TYPE: DNA
<213> ORGANISM: Artificial sequence
<220> FEATURE:
<223> OTHER INFORMATION: Synthetic Primer

<400> SEQUENCE: 92
tggggattta ccac                                                    14

<210> SEQ ID NO 93
<211> LENGTH: 14
<212> TYPE: DNA
<213> ORGANISM: Artificial sequence
<220> FEATURE:
<223> OTHER INFORMATION: Synthetic Primer

<400> SEQUENCE: 93
ggggttcacc acac                                                    14

<210> SEQ ID NO 94
<211> LENGTH: 17
<212> TYPE: DNA
<213> ORGANISM: Artificial sequence
<220> FEATURE:
<223> OTHER INFORMATION: Synthetic Primer

<400> SEQUENCE: 94
gggatttacc acaccag                                                 17

<210> SEQ ID NO 95
<211> LENGTH: 17
<212> TYPE: DNA
<213> ORGANISM: Artificial sequence
<220> FEATURE:
<223> OTHER INFORMATION: Synthetic Primer

<400> SEQUENCE: 95
gggatttacc acaccag                                                 17

<210> SEQ ID NO 96
<211> LENGTH: 17
<212> TYPE: DNA
<213> ORGANISM: Artificial sequence
<220> FEATURE:
<223> OTHER INFORMATION: Synthetic Primer

<400> SEQUENCE: 96
tggggactta ccacacc                                                 17

<210> SEQ ID NO 97
<211> LENGTH: 17
<212> TYPE: DNA
<213> ORGANISM: Artificial sequence
<220> FEATURE:
<223> OTHER INFORMATION: Synthetic Primer

<400> SEQUENCE: 97 tggggggttta ccacacc                                                17

<210> SEQ ID NO 98
<211> LENGTH: 17
```

```
<212> TYPE: DNA
<213> ORGANISM: Artificial sequence
<220> FEATURE:
<223> OTHER INFORMATION: Synthetic Primer

<400> SEQUENCE: 98
gggatttact acaccag                                                    17

<210> SEQ ID NO 99
<211> LENGTH: 14
<212> TYPE: DNA
<213> ORGANISM: Artificial sequence
<220> FEATURE:
<223> OTHER INFORMATION: Synthetic Primer

<400> SEQUENCE: 99
gggattaacc acac                                                       14

<210> SEQ ID NO 100
<211> LENGTH: 14
<212> TYPE: DNA
<213> ORGANISM: Artificial sequence
<220> FEATURE:
<223> OTHER INFORMATION: Synthetic Primer

<400> SEQUENCE: 100
ggggattaac caca                                                       14

<210> SEQ ID NO 101
<211> LENGTH: 15
<212> TYPE: DNA
<213> ORGANISM: Artificial sequence
<220> FEATURE:
<223> OTHER INFORMATION: Synthetic Primer

<400> SEQUENCE: 101
tggggattaa ccaca                                                      15

<210> SEQ ID NO 102
<211> LENGTH: 14
<212> TYPE: DNA
<213> ORGANISM: Artificial sequence
<220> FEATURE:
<223> OTHER INFORMATION: Synthetic Primer

<400> SEQUENCE: 102
gggggttaac caca                                                       14

<210> SEQ ID NO 103
<211> LENGTH: 14
<212> TYPE: DNA
<213> ORGANISM: Artificial sequence
<220> FEATURE:
<223> OTHER INFORMATION: Synthetic Primer

<400> SEQUENCE: 103
ggggttaacc acac                                                       14

<210> SEQ ID NO 104
<211> LENGTH: 14
<212> TYPE: DNA
<213> ORGANISM: Artificial sequence
<220> FEATURE:
<223> OTHER INFORMATION: Synthetic Primer

<400> SEQUENCE: 104
```
tgggggttaa ccac                                                  14

<210> SEQ ID NO 105
<211> LENGTH: 14
<212> TYPE: DNA
<213> ORGANISM: Artificial sequence
<220> FEATURE:
<223> OTHER INFORMATION: Synthetic Primer

<400> SEQUENCE: 105
gggattgacc acac                                                  14

<210> SEQ ID NO 106
<211> LENGTH: 14
<212> TYPE: DNA
<213> ORGANISM: Artificial sequence
<220> FEATURE:
<223> OTHER INFORMATION: Synthetic Primer

<400> SEQUENCE: 106
ggattgacca cacc                                                  14

<210> SEQ ID NO 107
<211> LENGTH: 13
<212> TYPE: DNA
<213> ORGANISM: Artificial sequence
<220> FEATURE:
<223> OTHER INFORMATION: Synthetic Primer

<400> SEQUENCE: 107
gggattgacc aca                                                   13

<210> SEQ ID NO 108
<211> LENGTH: 13
<212> TYPE: DNA
<213> ORGANISM: Artificial sequence
<220> FEATURE:
<223> OTHER INFORMATION: Synthetic Primer

<400> SEQUENCE: 108
gggactgacc aca                                                   13

<210> SEQ ID NO 109
<211> LENGTH: 14
<212> TYPE: DNA
<213> ORGANISM: Artificial sequence
<220> FEATURE:
<223> OTHER INFORMATION: Synthetic Primer

<400> SEQUENCE: 109
gggactgacc acac                                                  14

<210> SEQ ID NO 110
<211> LENGTH: 15
<212> TYPE: DNA
<213> ORGANISM: Artificial sequence
<220> FEATURE:
<223> OTHER INFORMATION: Synthetic Primer

<400> SEQUENCE: 110
tgggggttaa ccaca                                                 15

<210> SEQ ID NO 111
<211> LENGTH: 15
<212> TYPE: DNA
<213> ORGANISM: Artificial sequence

```
<220> FEATURE:
<223> OTHER INFORMATION: Synthetic Primer

<400> SEQUENCE: 111
tgtggttaac cccca                                                    15

<210> SEQ ID NO 112
<211> LENGTH: 14
<212> TYPE: DNA
<213> ORGANISM: Artificial sequence
<220> FEATURE:
<223> OTHER INFORMATION: Synthetic Primer

<400> SEQUENCE: 112
ggggcttacc acac                                                     14

<210> SEQ ID NO 113
<211> LENGTH: 14
<212> TYPE: DNA
<213> ORGANISM: Artificial sequence
<220> FEATURE:
<223> OTHER INFORMATION: Synthetic Primer

<400> SEQUENCE: 113
ggactttaca cacc                                                     14

<210> SEQ ID NO 114
<211> LENGTH: 14
<212> TYPE: DNA
<213> ORGANISM: Artificial sequence
<220> FEATURE:
<223> OTHER INFORMATION: Synthetic Primer

<400> SEQUENCE: 114
gggttttaca cacc                                                     14

<210> SEQ ID NO 115
<211> LENGTH: 15
<212> TYPE: DNA
<213> ORGANISM: Artificial sequence
<220> FEATURE:
<223> OTHER INFORMATION: Synthetic Primer

<400> SEQUENCE: 115
ggatttttca cacca                                                    15

<210> SEQ ID NO 116
<211> LENGTH: 14
<212> TYPE: DNA
<213> ORGANISM: Artificial sequence
<220> FEATURE:
<223> OTHER INFORMATION: Synthetic Primer

<400> SEQUENCE: 116
ggattttaca cacc                                                     14

<210> SEQ ID NO 117
<211> LENGTH: 17
<212> TYPE: DNA
<213> ORGANISM: Artificial sequence
<220> FEATURE:
<223> OTHER INFORMATION: Synthetic Primer

<400> SEQUENCE: 117
gggattttac acaccag                                                  17
```

-continued

<210> SEQ ID NO 118
<211> LENGTH: 17
<212> TYPE: DNA
<213> ORGANISM: Artificial sequence
<220> FEATURE:
<223> OTHER INFORMATION: Synthetic Primer

<400> SEQUENCE: 118 gggattttc acaccag                                                    17

<210> SEQ ID NO 119
<211> LENGTH: 14
<212> TYPE: DNA
<213> ORGANISM: Artificial sequence
<220> FEATURE:
<223> OTHER INFORMATION: Synthetic Primer

<400> SEQUENCE: 119
gggattttac acac                                                      14

<210> SEQ ID NO 120
<211> LENGTH: 14
<212> TYPE: DNA
<213> ORGANISM: Artificial sequence
<220> FEATURE:
<223> OTHER INFORMATION: Synthetic Primer

<400> SEQUENCE: 120
ggggatttta caca                                                      14

<210> SEQ ID NO 121
<211> LENGTH: 14
<212> TYPE: DNA
<213> ORGANISM: Artificial sequence
<220> FEATURE:
<223> OTHER INFORMATION: Synthetic Primer

<400> SEQUENCE: 121
ccctaaaatg tgtg                                                      14

<210> SEQ ID NO 122
<211> LENGTH: 14
<212> TYPE: DNA
<213> ORGANISM: Artificial sequence
<220> FEATURE:
<223> OTHER INFORMATION: Synthetic Primer

<400> SEQUENCE: 122 ggattttca cacc                                                       14

<210> SEQ ID NO 123
<211> LENGTH: 14
<212> TYPE: DNA
<213> ORGANISM: Artificial sequence
<220> FEATURE:
<223> OTHER INFORMATION: Synthetic Primer

<400> SEQUENCE: 123 gattttcac acca                                                       14

<210> SEQ ID NO 124
<211> LENGTH: 14
<212> TYPE: DNA
<213> ORGANISM: Artificial sequence
<220> FEATURE:
<223> OTHER INFORMATION: Synthetic Primer

```
<400> SEQUENCE: 124
gggatttttc acac                                                 14

<210> SEQ ID NO 125
<211> LENGTH: 14
<212> TYPE: DNA
<213> ORGANISM: Artificial sequence
<220> FEATURE:
<223> OTHER INFORMATION: Synthetic Primer

<400> SEQUENCE: 125
cccctaaaat gtgt                                                 14

<210> SEQ ID NO 126
<211> LENGTH: 14
<212> TYPE: DNA
<213> ORGANISM: Artificial sequence
<220> FEATURE:
<223> OTHER INFORMATION: Synthetic Primer

<400> SEQUENCE: 126
ggttttatac acca                                                 14

<210> SEQ ID NO 127
<211> LENGTH: 14
<212> TYPE: DNA
<213> ORGANISM: Artificial sequence
<220> FEATURE:
<223> OTHER INFORMATION: Synthetic Primer

<400> SEQUENCE: 127
gggttttata cacc                                                 14

<210> SEQ ID NO 128
<211> LENGTH: 14
<212> TYPE: DNA
<213> ORGANISM: Artificial sequence
<220> FEATURE:
<223> OTHER INFORMATION: Synthetic Primer

<400> SEQUENCE: 128
ggggttttat acac                                                 14

<210> SEQ ID NO 129
<211> LENGTH: 14
<212> TYPE: DNA
<213> ORGANISM: Artificial sequence
<220> FEATURE:
<223> OTHER INFORMATION: Synthetic Primer

<400> SEQUENCE: 129
gggggcttac caca                                                 14

<210> SEQ ID NO 130
<211> LENGTH: 14
<212> TYPE: DNA
<213> ORGANISM: Artificial sequence
<220> FEATURE:
<223> OTHER INFORMATION: Synthetic Primer

<400> SEQUENCE: 130
ggattctaca cacc                                                 14

<210> SEQ ID NO 131
```

```
<211> LENGTH: 13
<212> TYPE: DNA
<213> ORGANISM: Artificial sequence
<220> FEATURE:
<223> OTHER INFORMATION: Synthetic Primer

<400> SEQUENCE: 131
gattctacac acc                                                        13

<210> SEQ ID NO 132
<211> LENGTH: 13
<212> TYPE: DNA
<213> ORGANISM: Artificial sequence
<220> FEATURE:
<223> OTHER INFORMATION: Synthetic Primer

<400> SEQUENCE: 132
ggattctaca cac                                                        13

<210> SEQ ID NO 133
<211> LENGTH: 14
<212> TYPE: DNA
<213> ORGANISM: Artificial sequence
<220> FEATURE:
<223> OTHER INFORMATION: Synthetic Primer

<400> SEQUENCE: 133
gggattctac acac                                                       14

<210> SEQ ID NO 134
<211> LENGTH: 14
<212> TYPE: DNA
<213> ORGANISM: Artificial sequence
<220> FEATURE:
<223> OTHER INFORMATION: Synthetic Primer

<400> SEQUENCE: 134
gggttttata cccc                                                       14

<210> SEQ ID NO 135
<211> LENGTH: 13
<212> TYPE: DNA
<213> ORGANISM: Artificial sequence
<220> FEATURE:
<223> OTHER INFORMATION: Synthetic Primer

<400> SEQUENCE: 135
ggttttatac ccc                                                        13

<210> SEQ ID NO 136
<211> LENGTH: 13
<212> TYPE: DNA
<213> ORGANISM: Artificial sequence
<220> FEATURE:
<223> OTHER INFORMATION: Synthetic Primer

<400> SEQUENCE: 136
gttttatacc cca                                                        13

<210> SEQ ID NO 137
<211> LENGTH: 15
<212> TYPE: DNA
<213> ORGANISM: Artificial sequence
<220> FEATURE:
<223> OTHER INFORMATION: Synthetic Primer

<400> SEQUENCE: 137
```

-continued accagacaaa aaaca                                                        15

<210> SEQ ID NO 138
<211> LENGTH: 14
<212> TYPE: DNA
<213> ORGANISM: Artificial sequence
<220> FEATURE:
<223> OTHER INFORMATION: Synthetic Primer

<400> SEQUENCE: 138
gggactgacc acac                                                         14

<210> SEQ ID NO 139
<211> LENGTH: 15
<212> TYPE: DNA
<213> ORGANISM: Artificial sequence
<220> FEATURE:
<223> OTHER INFORMATION: Synthetic Primer

<400> SEQUENCE: 139
caccagacaa aaaac                                                        15

<210> SEQ ID NO 140
<211> LENGTH: 14
<212> TYPE: DNA
<213> ORGANISM: Artificial sequence
<220> FEATURE:
<223> OTHER INFORMATION: Synthetic Primer

<400> SEQUENCE: 140
cagacaagaa acat                                                         14

<210> SEQ ID NO 141
<211> LENGTH: 14
<212> TYPE: DNA
<213> ORGANISM: Artificial sequence
<220> FEATURE:
<223> OTHER INFORMATION: Synthetic Primer

<400> SEQUENCE: 141
ccagacaaga aaca                                                         14

<210> SEQ ID NO 142
<211> LENGTH: 15
<212> TYPE: DNA
<213> ORGANISM: Artificial sequence
<220> FEATURE:
<223> OTHER INFORMATION: Synthetic Primer

<400> SEQUENCE: 142
accagacaag aaaca                                                        15

<210> SEQ ID NO 143
<211> LENGTH: 14
<212> TYPE: DNA
<213> ORGANISM: Artificial sequence
<220> FEATURE:
<223> OTHER INFORMATION: Synthetic Primer

<400> SEQUENCE: 143
agacaaaaag catc                                                         14

<210> SEQ ID NO 144
<211> LENGTH: 14
<212> TYPE: DNA

```
<213> ORGANISM: Artificial sequence
<220> FEATURE:
<223> OTHER INFORMATION: Synthetic Primer

<400> SEQUENCE: 144
cagacaaaaa gcat                                                    14

<210> SEQ ID NO 145
<211> LENGTH: 15
<212> TYPE: DNA
<213> ORGANISM: Artificial sequence
<220> FEATURE:
<223> OTHER INFORMATION: Synthetic Primer

<400> SEQUENCE: 145
cagacaaaaa gcatc                                                   15

<210> SEQ ID NO 146
<211> LENGTH: 14
<212> TYPE: DNA
<213> ORGANISM: Artificial sequence
<220> FEATURE:
<223> OTHER INFORMATION: Synthetic Primer

<400> SEQUENCE: 146
ccagataaaa aaca                                                    14

<210> SEQ ID NO 147
<211> LENGTH: 14
<212> TYPE: DNA
<213> ORGANISM: Artificial sequence
<220> FEATURE:
<223> OTHER INFORMATION: Synthetic Primer

<400> SEQUENCE: 147
accagataaa aaac                                                    14

<210> SEQ ID NO 148
<211> LENGTH: 15
<212> TYPE: DNA
<213> ORGANISM: Artificial sequence
<220> FEATURE:
<223> OTHER INFORMATION: Synthetic Primer

<400> SEQUENCE: 148
cccagataaa aaaca                                                   15

<210> SEQ ID NO 149
<211> LENGTH: 16
<212> TYPE: DNA
<213> ORGANISM: Artificial sequence
<220> FEATURE:
<223> OTHER INFORMATION: Synthetic Primer

<400> SEQUENCE: 149
ccagataaaa aacatc                                                  16

<210> SEQ ID NO 150
<211> LENGTH: 15
<212> TYPE: DNA
<213> ORGANISM: Artificial sequence
<220> FEATURE:
<223> OTHER INFORMATION: Synthetic Primer

<400> SEQUENCE: 150
caccagataa aaaac                                                   15
```

```
<210> SEQ ID NO 151
<211> LENGTH: 15
<212> TYPE: DNA
<213> ORGANISM: Artificial sequence
<220> FEATURE:
<223> OTHER INFORMATION: Synthetic Primer

<400> SEQUENCE: 151
cagacaagaa acatc                                                     15

<210> SEQ ID NO 152
<211> LENGTH: 14
<212> TYPE: DNA
<213> ORGANISM: Artificial sequence
<220> FEATURE:
<223> OTHER INFORMATION: Synthetic Primer

<400> SEQUENCE: 152
accagacaag aaac                                                      14

<210> SEQ ID NO 153
<211> LENGTH: 15
<212> TYPE: DNA
<213> ORGANISM: Artificial sequence
<220> FEATURE:
<223> OTHER INFORMATION: Synthetic Primer

<400> SEQUENCE: 153
accagaccaa aaaca                                                     15

<210> SEQ ID NO 154
<211> LENGTH: 15
<212> TYPE: DNA
<213> ORGANISM: Artificial sequence
<220> FEATURE:
<223> OTHER INFORMATION: Synthetic Primer

<400> SEQUENCE: 154
accagacgaa aaaca                                                     15

<210> SEQ ID NO 155
<211> LENGTH: 15
<212> TYPE: DNA
<213> ORGANISM: Artificial sequence
<220> FEATURE:
<223> OTHER INFORMATION: Synthetic Primer

<400> SEQUENCE: 155
accagatcaa aaaca                                                     15

<210> SEQ ID NO 156
<211> LENGTH: 14
<212> TYPE: DNA
<213> ORGANISM: Artificial sequence
<220> FEATURE:
<223> OTHER INFORMATION: Synthetic Primer

<400> SEQUENCE: 156
accagatcaa aaac                                                      14

<210> SEQ ID NO 157
<211> LENGTH: 15
<212> TYPE: DNA
<213> ORGANISM: Artificial sequence
<220> FEATURE:
```

<223> OTHER INFORMATION: Synthetic Primer

<400> SEQUENCE: 157
caccagatca aaaac                                            15

<210> SEQ ID NO 158
<211> LENGTH: 14
<212> TYPE: DNA
<213> ORGANISM: Artificial sequence
<220> FEATURE:
<223> OTHER INFORMATION: Synthetic Primer

<400> SEQUENCE: 158
accagacgaa aaac                                             14

<210> SEQ ID NO 159
<211> LENGTH: 14
<212> TYPE: DNA
<213> ORGANISM: Artificial sequence
<220> FEATURE:
<223> OTHER INFORMATION: Synthetic Primer

<400> SEQUENCE: 159
ccagacgaaa aaca                                             14

<210> SEQ ID NO 160
<211> LENGTH: 14
<212> TYPE: DNA
<213> ORGANISM: Artificial sequence
<220> FEATURE:
<223> OTHER INFORMATION: Synthetic Primer

<400> SEQUENCE: 160
ccagaccaaa aaca                                             14

<210> SEQ ID NO 161
<211> LENGTH: 14
<212> TYPE: DNA
<213> ORGANISM: Artificial sequence
<220> FEATURE:
<223> OTHER INFORMATION: Synthetic Primer

<400> SEQUENCE: 161
accagaccaa aaac                                             14

<210> SEQ ID NO 162
<211> LENGTH: 29
<212> TYPE: DNA
<213> ORGANISM: Artificial sequence
<220> FEATURE:
<223> OTHER INFORMATION: Synthetic Primer

<400> SEQUENCE: 162
gtacagtatt agtaggacct acacctgtc                             29

<210> SEQ ID NO 163
<211> LENGTH: 29
<212> TYPE: DNA
<213> ORGANISM: Artificial sequence
<220> FEATURE:
<223> OTHER INFORMATION: Synthetic Primer

<400> SEQUENCE: 163
ccaaaagtta aacaatggcc attgacaga                             29

```
<210> SEQ ID NO 164
<211> LENGTH: 20
<212> TYPE: DNA
<213> ORGANISM: Artificial sequence
<220> FEATURE:
<223> OTHER INFORMATION: Synthetic Primer

<400> SEQUENCE: 164
agttcataac ccatccaaag                                            20
```

METHOD FOR DETECTION OF DRUG-INDUCED MUTATIONS IN THE REVERSE TRANSCRIPTASE GENE This is a divisional of application Ser. No. 09/580,794, filed May 30, 2000, U.S. Pat. No. 6,331,389, which is a divisional of Ser. No. 08/913,833, filed Sep. 15, 1997, U.S. Pat. No. 6,087,093, which is a 371 national application of PCT/EP97/00211 filed Jan. 17, 1997, which claims priority under 35 USC 119 to EP 96 870081.5 filed Jun. 25, 1996 and EP 96 870005.4 filed Jan. 28, 1996.

BACKGROUND OF THE INVENTION

The present invention relates to the field of HIV diagnosis. More particularly, the present invention relates to the field of diagnosing the susceptibility of an HIV sample to antiviral drugs used to treat HIV infection.

The present invention relates to a method for the rapid and reliable detection of drug-induced mutations in the HIV reverse transcriptase gene allowing the simultaneous characterization of a range of codons involved in drug resistance using specific sets of probes optimized to function together in a reverse-hybridisation assay.

During the treatment of human immunodeficiency virus (HIV) type 1 infected individuals with antiretroviral nucleoside analogs emergence of resistance against these drugs has been observed. The mechanism responsible for the resistance is not fully understood, since the appearance of a resistant virus in not always correlated with clinical deterioration (Boucher et al. 1992). Amongst the reverse transcriptase (RT) inhibitors, the nucleoside analogs 3'-azido-2',3'-dideoxyThymidine (AZT, Zidovudine), 2',3'-dideoxyInosine (ddI), 2',3'-dideoxyCytidine (ddC), (−)-β-L-2',3'-dideoxy-3'-thioCytidine (3TC), 2',3'-didehydro-3'deoxyThymidine (D4T) and (−)-2'3'-dideoxy-5-fluoro-3'-thiacytidine (FTC) are the most important, since they show a favourable ratio of toxicity for the host versus efficacy as antiviral. All these compounds act in a similar way, namely they serve, after intracellular phosphorylation, as chain terminators of the RT reaction. Upon prolonged treatment with these nucleoside analogs, accumulation of mutations in the viral reverse transcriptase gene (RT) occur, thereby escaping the inhibitory effect of the antivirals. The most important mutations induced by the above compounds and leading to gradually increasing resistance were found at amino acid (aa) positions 41 (M to L), 69 (T to D), 70 (K to R), 74 (L to V), 181 (Y to C), 184 (M to V) and 215 (T to Y or F) (Schinazi et al., 1994). Mutations at aa 65, 67, 75 and 219 have also been reported but these were only showing a minor decrease in sensitivity. More recently, multi-drug-resistant HIV-1 strains were described showing aa changes at codon 62, 75, 77, 116, and 151 (Iversen et al., 1996). In general, these aa changes are the consequence of single point mutations at the first or second codon letter, but in the case of T69D (ACT to GAT), T215Y (ACC to TAC) and T215F (ACC to TTC),: two nucleotide mutations are necessarry. Whether in these cases the single nucleotide mutation intermediates exist, and if they show any importance in the mechanism for acquiring resistance is as yet not reported. Third letter variations are in general not leading to an amino acid change, and are therefore seen as natural polymorphisms.

The regime for an efficient antiviral treatment is not clear at all. The appearance of one or several of these mutations during antiviral treatment need to be interpreted in conjunction with the virus load and the amount of CD4 cells. Indeed, since it has been shown that the effect of AZT resistance mutations can be suppressed after the appeareance of the 3TC induced M184V mutation, it is clear that disease progression is multifactorial. The influence of other simultaneous occuring mutations under different combination therapies with respect to the outcome and resistance of the virus has not yet been analysed systematically. In order to get a better insight into the mechanisms of resistance and HIV biology, it is necessarry to analyse follow-up plasma samples of antiviral treated patients for these mutational events together with the simultaneous occuring changes of virus titre and CD4 cells.

BRIEF SUMMARY OF THE INVENTION

It is an aim of the present invention to develop a rapid and reliable detection method for determination of the antiviral drug resistance of viruses which contain reverse transcriptase genes such as HIV retroviruses and Hepadnaviridae present in a biological sample.

More particularly it is an aim of the present invention to provide a genotyping assay allowing the detection of the different HIV RT gene wild type and mutation codons involved in the antiviral resistance in one single experiment.

It is also an aim of the present invention to provide an HIV RT genotyping assay or method which allows to infer the nucleotide sequence at codons of interest and/or the amino acids at the codons of interest and/or the antiviral drug resistance spectrum, and possibly also infer the HIV type or subtype isolate involved.

Even more particularly it is an aim of the present invention to provide a genotyping assay allowing the detection of the different HIV RT gene polymorphisms representing wild-type and mutation codons in one single experimental setup.

It is another aim of the present invention to select particular probes able to discriminate wild-type HIV RT sequences from mutated or polymorphic HIV RT sequences conferring resistance to one or more antiviral drugs, such as AZT, ddI, ddC, 3TC or FTC, D4T or others.

It is more particularly an aim of the present invention to select particular probes able to discriminate wild-type HIV RT sequences from mutated or polymorphic HIV RT sequences conferring resistance to AZT.

It is more particularly an aim of the present invention to select particular probes able to discriminate wild-type HIV RT sequences from mutated HIV RT sequences conferring resistance to ddI.

It is more particularly an aim of the present invention to select particular probes able to discriminate wild-type HIV RT sequences from mutated HIV RT sequences conferring resistance to ddC.

It is more particularly an aim of the present invention to select particular probes able to discriminate wild-type HIV RT sequences from mutated HIV RT sequences conferring resistance to 3TC.

It is more particularly an aim of the present invention to select particular probes able to discriminate wild-type HIV RT sequences from mutated HIV RT sequences conferring resistance to D4T.

It is more particularly an aim of the present invention to select particular probes able to discriminate wild-type HIV RT sequences from mutated HIV RT sequences conferring resistance to FTC.

It is more particularly an aim of the present invention to select particular probes able to discriminate wild-type HIV RT sequences from mutated HIV RT sequences conferring resistance to multiple nucleoside analogues (i.e. multidrug resistance).

It is more particularly an aim of the

Table 4. For several probes multiple reference panel possibilities are available, but only one relevant accession number given each time. On top of the strips, the amino acids at the relevant codon, as derived from the probe reactivity, is indicated.

Figure 2F:
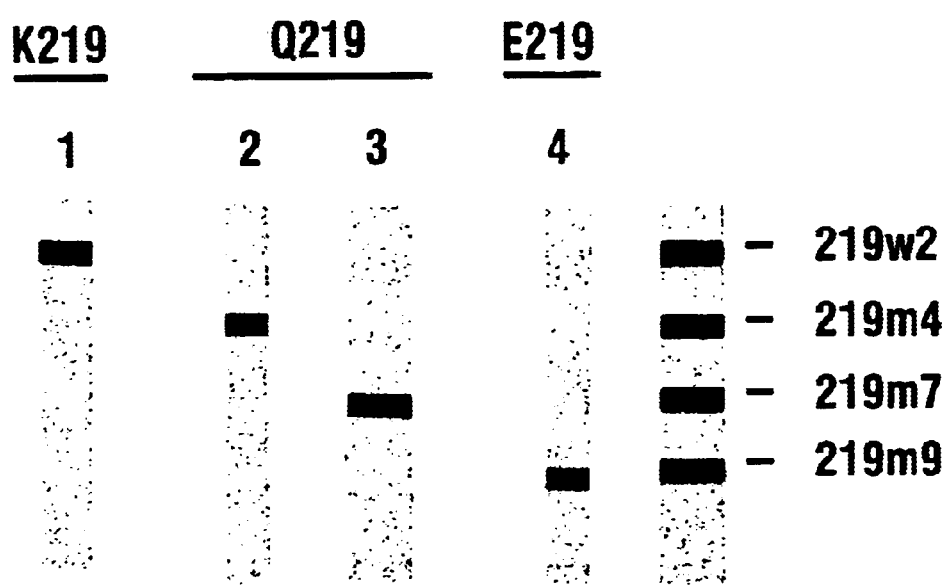

FIG. 2F. Reactivities of the selected probes for codons 219 immobilized on LiPA strips with reference material. The position of each probe on the membrane strip is shown at the right of each panel. The sequence of the relevant part of the selected probes is given in Table 4. Each strip is incubated with a biotinylated PCR fragment from the reference panel. The reference panel accession numbers are indicated in Table 4. For several probes multiple reference panel possibilities are available, but only one relevant accession number given each time. On top of the strips, the amino acids at the relevant codon, as derived from the probe reactivity, is indicated.

FIGS. 3A–3I. Clinical and virological features detectable in three patient follow-up samples. All three patients were infected with a HIV-1 strain showing the M41-T69-K70-L74-V75-M184-F214-T215-K219 genotype (wild type pattern). 3A, 3D, and 3G: Fluctuations between plasma HIV RNA copy numbers (■) and CD4 cell count (x) are given in function of time. The different treatment regimens and the period of treatment is indicated on top. 3B, 3E, and 3H: Changes that appeared during the treatment period and that could be scored by means of the LiPA probes are indicated, for patient 91007 at codon 41 and 215; for patient 94013 at codon 184; for patient 92021 at codon 70, 214, 215, 219. 3C, 3F, and 3I. Corresponding LiPA strips for a subset of the aa changes are shown. LiPA probes are indicated on the left, the as interpretation is indicated at the right of each panel.

Figure 4:
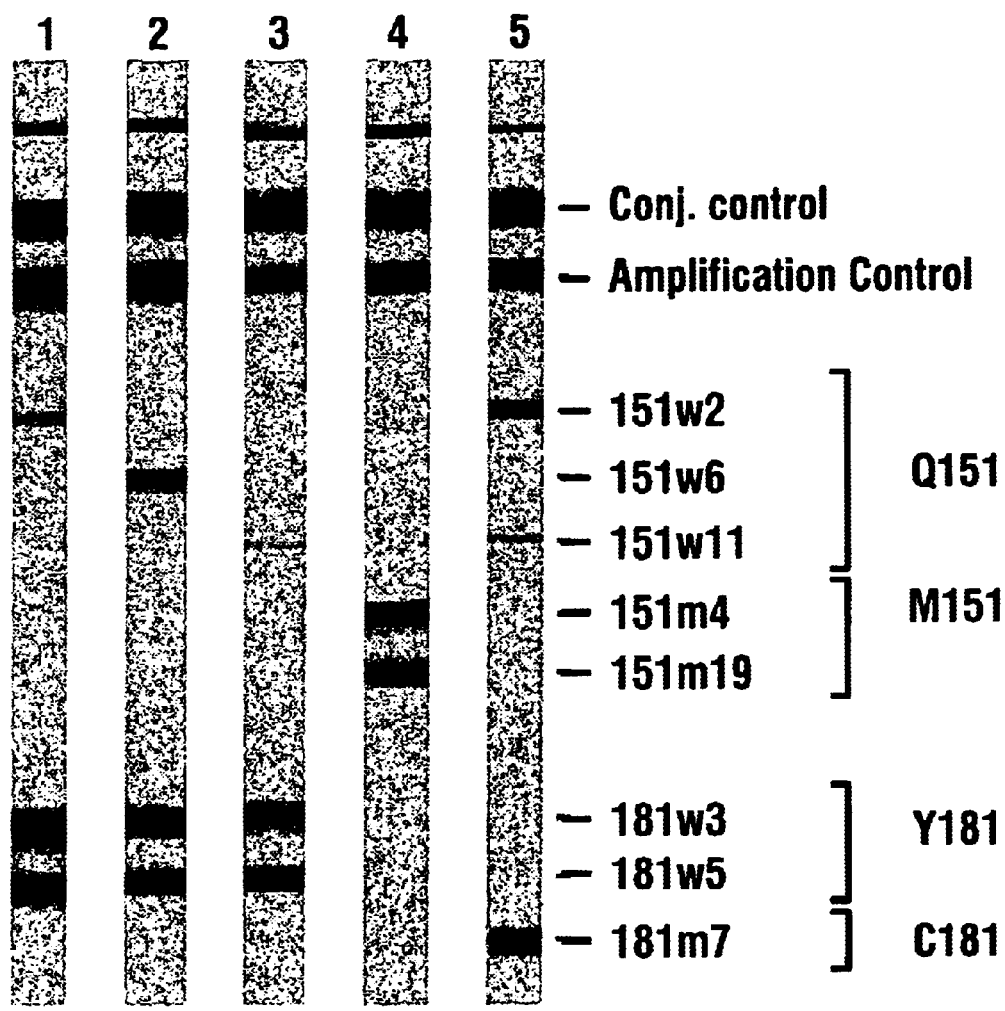

FIG. 4. Reactivities of the selected probes for codons 151 and 181 on LiPA strips with reference material. The position of each probe on the membrane strip is shown at the right of each panel. The sequence of the relevant part of the selected probes is given in Table 3. LiPA strips were incubated with sequence-confirmed PCR fragments, extracted and amplified from: a wild-type HIV-1 isolate (strip 1), a wild-type isolate with a polymorphism at codon 151 (strip 2) or 149 (strip 3), a multi-drug resistant HIV-1 isolate (strip 4) with no information about codon 181 and a non-nucleoside analogue treated HIV-1 isolate which remained wild-type at codon 151 (strip 5).

DETAILED DESCRIPTION OF THE INVENTION

According to a preferred embodiment of the present invention, step (iii) is performed using a set of at least 2, preferably at least 3, more preferably at least 4 and most preferably at least 5 probes meticulously designed as such that they show the desired hybridization results, when used in a reverse hybridisation assay format, more particularly under the same hybridization and wash conditions.

According to a preferred embodiment, the present invention relates to a set of at least 2 probes each targetting one or more of the nucleoside RT inhibitor induced nucleotide changes or target sequences including such a nucleotide change as indicated in any of FIG. 1 or Tables 1, 2 or 4. The numbering of HIV-1 RT gene encoded amino acids is as generally accepted in literature.

More prefererably, the present invention relates to a set of two or more probes each targetting two, three, four, five or more different nucleoside RT inhibitor induced nucleotide changes as indicated in any of FIG. 1 or Tables 1, 2 or 4.

More particularly, the present invention relates to a set of at least 2 probes allowing the characterization of a wild-type, polymorphic or mutated codon at any one of the drug-induced mutation positions represented in any of FIG. 1 or Tables 1 or 2 or at any one of the polymorphic positions represented in Table 4.

Even more particularly, the present invention relates to a set of at least 2 probes allowing the characterization of a wild-type, polymorphic or mutated codon at any of the positions represented in FIG. 1.

All the above mentioned sets of probes have as a common characteristic that all the probes in said set are designed so that they can function together in a reverse-hybridization assay, more particularly under similar hybridization and wash conditions.

A particularly preferred set of probes selected out of the probes with SEQ ID NO 1 to 161 of Table 3 is described in example 2.2 and is indicated in Table 4 and FIG. 2. The particularly selected probes are also indicated in Table 3.

A particularly preferred embodiment of the present invention is a method for determining the susceptibility to antiviral drugs of an HIV isolates in a sample using a set of probes as defined above, wherein said set of probes is characterized as being chosen such that for a given mutation disclosed in any of FIG. 1, or Tables 1, 2 or 4 the following probes are included in said set at least one probe for detecting the presence of drug induced mutation at said position;

at least one probe for detecting the presence of a wild-type sequence at said position;

preferably also (an) additional probe(s) for detecting wild-type polymorphisms at positions surrounding the mutation position.

Inclusion of the latter two types of probes greatly contributes to increasing the sensitivity of said assays as demonstrated in the examples section.

A particularly preferred set of probes in this respect is shown in Tables 3 and 4 and FIGS. 2 and 3.

Selected sets of probes according to the present invention include at least one probe, preferably at least two probes, characterizing the presence of a drug-induced mutation in a codon position chosen from the following list of codons susceptible to mutations in the HIV RT gene: 41, 50, 67, 69, 70, 74, 75, 151, 181, 184, 215 or 219. Said probes being characterized in that they can function in a method as set out above.

Also selected probes according to the present invention are probes which allow to differentiate any of the nucleotide changes as represented in any of FIG. 1 or Tables 1, 2 or 4. Said probes being characterized in that they can function in a method as set out above.

Also selected sets of probes for use in a method according to the present invention include at least one, preferably at least two (sets of) probes, with said probes characterizing the presence of a drug-induced mutation in two codon positions chosen from the following list of codon combinations, with said codons being susceptible to mutations in the HIV RT gene: 41 and/or 50; 41 and/or 67; 41 and/or 69; 41 and/or 70; 41 and/or 74; 41 and/or 75; 41 and/or 151; 1 and/or 181; 41 and/or 184; 41 and/or 215; 41 and/or 219; 50 and/or 67; 50 and/or 69; 50 and/or 70; 50 and/or 74; 50 and/or 75; 50 and/or 75; 50 and/or 151; 50 and/or 181; 50 and/or 184; 50 and/or 215; 50 and/or 219; 67 and/or 69; 67 and/or 70; 67 and/or 74; 67 and/or 75; 67 and/or 151; 67 and/or 181; 67 and/or 184; 67 and/or 215; 67 and/or 219; 69 and/or 70; 69 and/or 74; 69 and/or 75; 69 and/or 151; 69 and/or 181; 69 and/or 184; 69 and/or 215; 69 and/or 219; 70 and/or 74; 70 and/or 75; 70 and/or 151; 70 and/or 181: 70 and/or 184; 70 and/or 215; 70 and/or 219: 74 and/or 75; 74 and/or 151; 74 and/or 181; 74 and/or 184; 74 and/or 215; 74 and/or 219; 75 and/or 151; 75 and/or 181; 75 and/or 184; 75 and/or 215; 75 and/or 219; 151 and/or 181: 151 and/or 184; 151 and/or 215; 151 and/or 219; 181 and/or 184; 181 and/or 215; 181 and/or 219; 184 and/or 215; 184 and/or 219; 215 and/or 219.

Even more preferred selected sets of probes for use in a method according to the present invention include in addition to the probes deemed above a third (set of) probe(s) characterizing the presence of a third drug-induced mutation at any of positions 41, 50, 67, 69, 70, 74, 75, 151, 181, 184, 215 or 219, or particular combinations thereof.

Particularly preferred is also a set of probes which allows simultaneous detection of antiviral resistance at codons 41, 50, 67, 69, 70, 74, 75, 151, 181, 184 and 215, possibly also at codon 219.

An additional embodiment of the present invention includes at least one probe, preferably at least two probes, characterizing the presence of a drug-induced mutation in codon positions chosen from the list of codons susceptible-to mutations in the HIV RT gene as mentioned in any of Table 1 or 2, such as at codons 65, 115, 150, 98, 100, 103, 106, 108, 188, 190, 138, 199, 101, 179, 236, 238 or 233, with said probes forming possibly part of a composition.

Particularly preferred embodiments of the invention thus include a set of probes for codon 41 comprising at least one, preferably at least two, probe(s) for targetting at least one, preferably at least two, nucleotide changes in any the following codons as represented in region I in FIG. 1:

wild-type codon E40 (GAA) or polymorphic codon E40 (GAG), mutant codon L41 (TTG) or L41 (CTG) or wild-type codon M41 (ATG), wild-type codon E42 (GAA) or polymorphic codon E42 (GAG), wild-type codon K43 (AAG) or polymorphic codon K43 (AAA) or polymorphic E43 (GAA).

Particularly preferred embodiments of the invention thus include a set of probes for codon 50 comprising at least one, preferably at least two, probe(s) for targetting at least one, preferably at least two, nucleotide changes in any the following codons as represented in region II in FIG. 1:

wild-type codon K49 (AAA) or polymorphic codon R49 (AGA), mutant codons V50 (GTT) or T50 (ACG), wild-type codon I50 (ATT) or polymorphic codon I50 (ATC).

Particularly preferred embodiments of the invention thus include a set of probes for codons 67–70 comprising at least one, preferably at least two, probe(s) for targetting at least one, preferably at least two, nucleotide changes in any of the following codons as represented in region III in FIG. 1:

wild-type K65 (AAA) or polymorphic K65 (AAG), wild-type K66 (AAA) or polymorphic K66 (AAG). wild-type D67 (GAC) or mutant N67 (AAC), wild-type T69 (ACT) or polymorphic T69 (ACA), mutant D69 (GAT) or N69 (AAT) or A69 (GCT), wild-type K70 (AAA), polymorphic K70 (AAG) or mutant R70 (AGA).

Particularly preferred embodiments of the present invention include a set of probes for codons 74–75 comprising at least one, preferably at least two, probes for targetting at least one, preferably at least two, nucleotide chances in any of the following codons as represented in region IV of FIG. 1:

wild-type K73 (AAA) or polymorphic K73 (AAG), wild-type L74 (TTA) or mutant V74 (GTA), wild-type V75 (GTA) or polymorphic V75 (GTG) or mutant T75 (ACA), wild-type D76 (GAT) or polymorphic D76 (GAC).

Particularly preferred embodiments of the present invention include a set of probes for codon 151 comprising at least one, preferably at least two, probes for targetting at least one, preferably at least two, nucleotide changes in any of the following codons as represented in region V of FIG. 1:

wild-type L149 (CTT) or polymorphic L149 (CTC) or L149 (CTG), wild-type P150 (CCA) or polymorphic P150 (CCG), wild-type Q151 (CAG) or mutant M151 (ATG) or L151 (CTG) or polymorphic Q151 (CAA).

Particularly preferred embodiments of the present invention include a set of probes for codon 181–184 comprising at least one, preferably at least two, probe(s) for targetting at least one, preferably at least two, nucleotide changes in any of the following codons as represented in region VI of FIG. 1:

wild-type Y181 (TAT) or mutant C181 (TGT), wild-type Q182 (CAA) or polymorphic Q182 (CAG), wild-type Y183 (TAC) or polymorphic Y183 (TAT), wild-type M184 (ATG) or mutant V184 (GTG) or I184 (ATA) or G184 (AGG), wild-type D185 (GAT) or polymorphic D185 (GAC), wild-type D186 (GAT) or polymorphic E186 (GAG), wild-type L187 (TTA) or polymorphic G187 (GGA) or V187 (GTA).

Particularly preferred embodiments of the present invention include a set of probes for codon 215 comprising at least one, preferably at least two, probe(s) for targetting at least one, preferably at least two, nucleotide changes in any of the following codons as represented in region VII of FIG. 1 wild-type G213 (GGA) or polymorphic G213 (GGG), wild-type F214 (TTT) or polymorphic F214 (TTC) or L214 (CTT) or L214 (TTA), wild-type T215 (ACC) or polymorphic T215 (ACT), mutant Y215 (TAC) or F215 (TTC).

Particularly preferred embodiments of the present invention include a set of probes for codon 219 comprising at least one, preferably at least two, probe(s) for targetting at least one, preferably at least two, nucleotide chances in any of the following codons as represented in region VIII of FIG. 1:

wild-type D218 (GAC) or polymorphic D218 (GAT), wild-type K219 (AAA) or polymorphic K219 (AAG) or mutant Q219 (CAA) or E219 (GAA), wild-type K220 (AAA) or polymorphic K220 (AAG).

Examples of probes of the invention are represented in Tables 3 and 4, and FIGS. 2 and 3. In Table 3, the probes withheld after selection are indicated using the letter "y". These probes of the invention are designed for attaining optimal performance under the same hybridization conditions so that they can be used in sets of at least 2 probes for simultaneous hybridization; this highly increases the usefulness of these probes and results in a significant gain in time and labour. Evidently, when other hybridization conditions would be preferred, all probes should be adapted accordingly by adding or deleting a number of nucleotides at their extremities. It should be understood that these concommitant adaptations should give rise to essentially the same result, namely that the respective probes still hybridize specifically with the defined target. Such adaptations might also be necessary if the amplified material should be RNA in nature and not DNA as in the case for the NASBA (nucleic acid sequence-based amplification) system.

The selection of the preferred probes of the present invention is based on a reverse hybridization assay using immobilized oligonucleotide probes present at distinct locations on a solid support. More particularly the selection of preferred probes of the present invention is based on the use of the Line Probe Assay (LiPA) principle which is a reverse hybridization assay using oligonucleotide probes immobilized as parallel lines on a solid support strip (Stuyver et al. 1993; international application WO 94/12670). This approach is particularly advantageous since it is fast and simple to perform. The reverse hybridization format and more particularly the LiPA approach has many practical advantages as compared to other DNA techniques or hybridization formats, especially when the use of a combination of probes is preferable or unavoidable to obtain the relevant information sought.

It is to be understood, however, that any other type of hybridization assay or format using any of the selected probes as described further in the invention, is also covered by the present invention.

The reverse hybridization approach implies that the probes are immnobilized to certain locations on a solid support and that the target DNA is labelled in order to enable the detection of the hybrids formed.

Methods for detecting nucleotide changes in RT genes of other viruses which have been found to harbour a pattern of drug-resistance mutation similar to the one observed for HIV based on the same principles as set out in the present invention should be understood as also being covered by the scope of the present invention.

The following definitions serve to illustrate the terms and expressions used in the present invention.

The term "antiviral drugs" refers particularly to an antiviral nucleoside analog or any other RT inhibitor. Examples of such antiviral drugs and the mutation they may cause in the HIV-RT gene are disclosed in Schinazi et al., 1994 and Mellors et al., 1995. The contents of the latter two documents particularly are to be considered as forming part of the present invention. The most important antiviral drugs focussed at in the present invention are disclosed in Tables 1 to 2.

The term "drug-induced mutation" refers to a mutation in the HIV RT gene which provokes a reduced susceptibility of the isolate to the respective drug.

The target material in the samples to be analysed may either be DNA or RNA, e.g.: genomic DNA, messenger RNA, viral RNA or amplified versions thereof. These molecules are also termed polynucleic acids.

It is possible to use genomic DNA or RNA molecules from HIV samples in the methods according to the present invention.

Well-known extraction and purification procedures are available for the isolation of RNA or DNA from a sample (f.i. in Maniatis et al., Molecular Cloning: A Laboratory Manual, 2nd Edition, Cold Spring Harbour Laboratory Press (1989)).

The term "probe" refers to single stranded sequence-specific oligonucleotides which have a sequence which is complementary to the target sequence to be detected.

The term "target sequence" as referred to in the present invention describes the nucleotide sequence of the wildtype, polymorphic or drug induced variant sequence of the RT gene to be specifically detected by a probe according to the present invention. This nucleotide sequence may encompass one or several nucleotide changes. Target sequences may refer to single nucleotide positions, codon positions, nucleotides encoding amino acids or to sequences spanning any of the foregoing nucleotide positions. In the present invention said target sequence often includes one or two variable nucleotide positions. It is to be understood that the complement of said target sequence is also a suitable target sequence in some cases. The target sequences as defined in the present invention provide sequences which should be complementary to the central part of the probe which is designed to hybridize specifically to said target region.

The term "complementary" as used herein means that the sequence of the single stranded probe is exactly the (inverse) complement of the sequence of the single-stranded target, with the target being defined as the sequence where the mutation to be detected is located.

Since the current application requires the detection of single basepair mismatches, very stringent conditions for hybridization are required, allowing in principle only hybridization of exactly complementary sequences. However, variations are possible in the length of the probes (see below), and it should be noted that, since the central part of the probe is essential for its hybridization characteristics, possible deviations of the probe sequence versus the target sequence may be allowable towards head and tail of the probe, when longer probe sequences are used. These variations, which may be conceived from the common knowledge in the art, should however always be evaluated experimentally, in order to check if they result in equivalent hybridization characteristics than the exactly complementary probes.

Preferably, the probes of the invention are about 5 to 50 nucleotides long, more preferably from about 10 to 25 nucleotides. Particularly preferred lengths of probes include 10, 11, 12, 13, 14, 15, 16, 17, 18, 19, 20, 21, 22, 23, 24 or 25 nucleotides. The nucleotides as used in the present invention may be ribonucleotides, deoxyribonucleotides and modified nucleotides such as inosine or nucleotides containing modified groups which do not essentially alter their hybridisation characteristics.

Probe sequences are represented throughout the specification as single stranded DNA oligonucleotides from the 5' to the 3' end. It is obvious to the man skilled in the art that any of the below-specified probes can be used as such, or in their complementary form, or in their RNA form (wherein T is replaced by U).

The probes according to the invention can be prepared by cloning of recombinant plasmids containing inserts including the corresponding nucleotide sequences, if need be by cleaving the latter out from the cloned plasmids upon using the adequate nucleases and recovering them, e.g. by fractionation according to molecular weight. The probes according to the present invention can also be synthesized chemically, for instance by the conventional phosphotriester method.

The term "solid support" can refer to any substrate to which an oligonucleotide probe can be coupled, provided that it retains its hybridization characteristics and provided that the background level of hybridization remains low. Usually the solid substrate will be a microtiter plate, a membrane (e.g. nylon or nitrocellulose) or a microsphere (bead) or a chip. Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin, haptens or proteins.

The term "labelled" refers to the use of labelled nucleic acids. Labelling may be carried out by the use of labelled nucleotides incorporated during the polymerase step of the amplification such as illustrated by Saiki et al. (1988) or Bej et al. (1990) or labelled primers, or by any other method known to the person skilled in the art. The nature of the label may be isotopic ($^{32}P$, $^{35}S$, etc.) or non-isotopic (biotin, digoxigenin, etc.).

The term "primer" refers to a single stranded oligonucleotide sequence capable of acting as a point of initiation for synthesis of a primer extension product which is complementary to the nucleic acid strand to be copied. The length and the sequence of the primer must be such that they allow to prime the synthesis of the extension products.

Preferably the primer is about 5–50 nucleotides long. Specific length and sequence will depend on the complexity of the required DNA or RNA targets, as well as on the conditions of primer use such as temperature and ionic strenght.

The fact that amplification primers do not have to match exactly with the corresponding template sequence to warrant proper amplification is amply documented in the literature (Kwok et al., 1990).

The amplification method used can be either polymerase chain reaction (PCR; Saiki et al., 1988), ligase chain reaction (LCR; Landgren et al., 1988; Wu & Wallace, 1989; Barany, 1991), nucleic acid sequence-based amplification (NASBA; Guatelli et al., 1990; Compton, 1991), transcription-based amplification system (TAS; Kwoh et al., 1989), strand displacement amplification (SDA; Duck, 1990; Walker et al., 1992) or amplification by means of Qβ replicase (Lizardi et al., 1988; Lomeli et al., 1989) or any other suitable method to amplify nucleic acid molecules known in the art.

The oligonucleotides used as primers or probes may also comprise nucleotide analogues such as phosphorothiates (Matsukura et al., 1987), alkylphosphorothiates (Miller et al., 1979) or peptide nucleic acids (Nielsen et al., 1991; Nielsen et al., 1993) or may contain intercalating agents (Asseline et al., 1984).

As most other variations or modifications introduced into the original DNA sequences of the invention these variations will necessitate adaptions with respect to the conditions under which the oligonucleotide should be used to obtain the required specificity and sensitivity. However the eventual results of hybridisation will be essentially the same as those obtained with the unmodified oligonucleotides.

The introduction of these modifications may be advantageous in order to positively influence characteristics such as hybridization kinetics, reversibility of the hybrid-formation, biological stability of the oligonucleotide molecules, etc.

The "sample" may be any biological material taken either directly from the infected human being (or animal), or after culturing (enrichment). Biological material may be e.g. expectorations of any kind, broncheolavages, blood, skin tissue, biopsies, sperm, lymphocyte blood culture material, colonies, liquid cultures, faecal samples, urine etc.

The sets of probes of the present invention will include at least 2, 3, 4, 5, 6, 7, 8, 9, 10, 11, 12, 13, 14, 15, 16, 17, 18, 19, 20, 21, 22, 23, 24, 25, 26, 27, 28, 29, 30 or more probes. Said probes may be applied in two or more distinct and known positions on a solid substrate. Often it is preferable to apply two or more probes together in one and the same position of said solid support.

For designing probes with desired characteristics, the following useful guidelines known to the person skilled in the art can be applied.

Because the extent and specificity of hybridization reactions such as those described herein are affected by a number of factors, manipulation of one or more of those factors will determine the exact sensitivity and specificity of a particular probe, whether perfectly complementary to its target or not. The importance and effect of various assay conditions, explained further herein, are known to those skilled in the art.

The stability of the nucleic acid hybrid should be chosen to be compatible with the assay conditions. This may be accomplished by avoiding long AT-rich sequences, by terminating the hybrids with G:C base pairs, and by designing the probe with an appropriate Tm. The beginning and end points of the probe should be chosen so that the length and %GC result in a Tm about 2–10° C. higher than the temperature at which the final assay will be performed. The base composition of the probe is significant because G-C base pairs exhibit greater thermal stability as compared to A-T base pairs due to additional hydrogen bonding. Thus, hybridization involving complementary nucleic acids of higher G-C content will be stable at higher temperatures.

Conditions such as ionic strenght and incubation temperature under which a probe will be used should also be taken into account when designing a probe. It is known that hybridization will increase as the ionic strenght of the reaction mixture increases, and that the thermal stability of the hybrids will increase with increasing ionic strenght. On the other hand, chemical reagents, such as formamide, urea, DMSO and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10–50 bases in length occurs approximately 5° C. below the melting temperature for a given duplex. Incubation at temperatures below the optimum may allow mismatched base sequences to hybridize and can therefore result in reduced specificity.

It is desirable to have probes which hybridize only under conditions of high stringency. Under high stringency conditions only highly complementary nucleic acid hybrids will form: hybrids without a sufficient degree of complementarity will not form. Accordingly, the stringency of the assay conditions determines the amount of complementarity needed between two nucleic acid strands forming a hybrid. The degree of stringency is chosen such as to maximize the difference in stability between the hybrid formed with the target and the nontarget nucleic acid. In the present case, single base pair changes need to be detected, which requires conditions of very high stringency.

The length of the target nucleic acid sequence and, accordingly, the length of the probe sequence can also be important. In some cases, there may be several sequences from a particular region, varying in location and length, which will yield probes with the desired hybridization characteristics. In other cases, one sequence may be significantly better than another which differs merely by a single base. While it is possible for nucleic acids that are not perfectly complementary to hybridize, the longest stretch of perfectly complementary base sequence will normally primarily determine hybrid stability. While oligonucleotide probes of different lengths and base composition may be used, preferred oligonucleotide probes of this invention are between about 5 to 50 (more particularely 10–25) bases in length and have a sufficient stretch in the sequence which is perfectly complementary to the target nucleic acid sequence.

Regions in the target DNA or RNA which are known to form strong internal structures inhibitory to hybridization are less preferred. Likewise, probes with extensive self-complementarity should be avoided. As explained above, hybridization is the association of two single strands of complementary nucleic acids to form a hydrogen bonded double strand. It is implicit that if one of the two strands is wholly or partially involved in a hybrid that it will be less able to participate in formation of a new hybrid. There can be intramolecular and intermolecular hybrids formed within the molecules of one type of probe if there is sufficient self complementarity. Such structures can be avoided through careful probe design. By designing a probe so that a substantial portion of the sequence of interest is single stranded, the rate and extent of hybridization may be greatly increased. Computer programs are available to search for this type of interaction. However, in certain instances, it may not be possible to avoid this type of interaction.

Standard hybridization and wash conditions are disclosed in the Materials & Methods section of the Examples. Other conditions are for instance 3×SSC (Sodium Saline Citrate), 20% deionized FA (Formamide) at 50° C.

Other solutions (SSPE (Sodium saline phosphate EDTA), TMACl (Tetramethyl ammonium Chloride), etc.) and temperatures can also be used provided that the specificity and sensitivity of the probes is maintained. If need be, slight modifications of the probes in length or in sequence have to be carried out to maintain the specificity and sensitivity required under the given circumstances.

In a more preferential embodiment, the above-mentioned polynucleic acids from step (i) or (ii) are hybridized with at least two, three, four, five, six, seven, eight, nine, ten, eleven, twelve, thirteen, fourteen, fifteen, sixteen, seventeen, eighteen, nineteen, twenty, or more of the above-mentioned target region specific probes, preferably with 5 or 6 probes, which, taken together, cover the "mutation region" of the RT gene.

The term "mutation region" means the region in the HIV RT gene sequence where most of the mutations responsible for antiviral drug resistance or other observed polymorphisms are located. A preferred part of this mutation region is represented in FIG. 1. This mutation region can be divided into 8 important parts: drug induced variations and polymorphisms located within aa positions 38 to 44 of RT gene, drug induced variations and polymorphisms located within aa positions 47 to 53 of RT gene, drug induced variations and polymorphisms located within aa positions 65 to 72 of the RT gene, drug induced variations and polymorphisms located within aa positions 73 to 77 of the RT gene, drug-induced variations and polymorphisms located within aa positions 148 to 154 of the RT gene, drug-induced variations and polymorphisms located within aa positions 180 to 187 of the RT gene, drug induced variations and polymorphisms located within aa positions 212 to 216 of the RT gene and drug induced variations and polymorphisms located within aa positions 217 to 220 of the RT gene.

Since some mutations may be more frequently occurring than others, e.g. in certain geographic areas or in specific circumstances (e.g. rather closed communities) it may be appropiate to screen only for specific mutations, using a selected set of probes as indicated above. This would result in a more simple test, which would cover the needs under certain circumstances.

In order to detect the antiviral drug RT resistance pattern with the selected set of oligonucleotide probes, any hybridization method known in the art can be used (conventional dot-blot, Southern blot, sandwich, etc.).

However, in order to obtain fast and easy results if a multitude of probes are involved, a reverse hybridization format may be most convenient.

In a preferred embodiment the selected set of probes are immobilized to a solid support in known distinct locations (dots, lines or other figures). In another preferred embodiment the selected set of probes are immobilized to a membrane strip in a line fashion. Said probes may be immobilized individually or as mixtures to delineated locations on the solid support.

A specific and very user-friendly embodiment of the above-mentioned preferential method is the LiPA method, where the above-mentioned set of probes is immobilized in parallel lines on a membrane, as further described in the examples.

The invention also provides for any probes and primer sets designed to specifically detect or amplify specifically these RT gene polymorphisms, and any method or kits using said primer and probes sets.

The invention further provides for any of the probes as described above, as well as compositions comprising at least one of these probes.

The invention also provides for a set of primers allowing amplification of the mutation region of the RT gene in general.

Primers may be labeled with a label of choice (e.g. biotine). Different primer-based target amplification systems may be used, and preferably PCR-amplification, as set out in the examples. Single-round or nested PCR may be used.

The invention also provides for a kit for inferring the nucleotide sequence at codons of interest in the HIV RT gene and/or the amino acids corresponding to these codons and/or the antiviral drug resistance spectrum of HIV isolates present in a biological sample comprising the following components:

(i) when appropiate, a means for releasing, isolating or concentrating the polynucleic acids present in said sample;
(ii) when appropriate, at least one of the above-defined set of primers;
(iii) at least two of the probes as defined above, possibly fixed to a solid support;
(iv) a hybridization buffer, or components necessary for producing said buffer;
(v) a wash solution, or components necessary for producing said solution;
(vi) when appropriate, a means for detecting the hybrids resulting from the preceding hybridization.
(vii) when appropriate, a means for attaching said probe to a solid support.

The term "hybridization buffer" means a buffer enabling a hybridization reaction to occur between the probes and the polynucleic acids present in the sample, or the amplified products, under the appropiate stringency conditions.

The term "wash solution" means a solution enabling washing of the hybrids formed under the appropiate stringency conditions.

A line probe assay (LiPA) was designed for the screening for variations at interesting amino acids in the HIV RT gene. The principle of the assay is based on reverse hybridization of an amplified polynucleic acid fragment such as a biotinylated PCR fragment of the HIV RT gene onto short oligonucleotides. The latter hybrid can then, via a biotine-streptavidine coupling, be detected with a non-radioactive colour developing system.

The present invention further relates to a reverse hybridization method wherein said oligonucleotide probes are immobilized, preferably on a membrane strip.

The present invention also relates to a composition comprising any of the probes as defined in Tables 3 and 4 or FIGS. 2 and 3.

The present invention relates also to a kit for inferring the HIV RT resistance spectrum of HIV in a biological sample, coupled to the identification of the HIV isolate L involved, comprising the following components:

(i) when appropiate, a means for releasing, isolating or concentrating the polynucleic acids present in the sample;
(ii) when appropriate, at least one of the sets of primers as defined above;

(iii) at least one of the probes as defined above, possibly fixed to a solid support;
(iv) a hybridization buffer, or components necessary for producing said buffer;
(v) a wash solution, or components necessary for producing said solution;
(vi) when appropriate, a means for detecting the hybrids resulting from the preceding hybridization;
(vii) when appropriate, a means for attaching said probe to a solid support The following examples only serve to illustrate the present invention. These examples are in no way intended to limit the scope of the present invention.

Table 1: Mutations in HIV-1 RT gene associated with resistance against nucleoside RT inhibitors. More details are given in Mellors et al., 1995.

Table 2: Mutations in HIV-1 RT gene associated with resistance against HIV-1 specific RT inhibitors. For more details see Mellors et al., 1995.

Abbreviations in Table 1 and 2:

AZT: 3'-azido-2'3'-dideoxythymidine
ddC: 2'3'-dideoxycytidine
ddI: 2'3'-dideoxyinosine
3TC: 3'dideoxy-3'-thiacytidine
FTC: 2'3'-dideoxy-5-fluoro-3'-thiacytidine
L'697,593: 5-ethyl-6-methyl-3-(2-phthalimido-ethyl)pyridin-2(1H)-one
L'697,661: 3-Il(-4,7-dichloro-1,3-benzoxazol-2-yl)methyl amino-5-ethyl-6-methylpyridin-2(1H)-one
Nevirapine: Il-cyclopropyl-5,11-dihydro-4-methyl-6H-dipyridol(3,2-b:2',3'-e)diazepin-6-one
TIBO R82150: (+)-(5S)-4,5,6,7,-tetrahydro-5-methyl-6-(3-methyl-2butenyl)imidazo(4,5,1-)k) (1,4)-benzodiazepin-2(1H)-thione
TIBO 82913: (+)-(5S)-4,5,6,7,-tetrahydro-9-chloro-5-methyl-6-(3-methyl-2-butenyl)imidazo(4,5,1kj)-(1,4)benzo-diazepin-2(1H)-thione
TSAO-m$^2$T: (2',5'-bis-o-(tert-buthyldimethylsilyl)-3'-spiro-5'-(4'-amino-1',2'-oxsathiole-2',2'-dioxide)
U90152: 1-(3-(1-methylethyl)-amino)-2-pyridinyl)4-(5-(methylsulphonyl)-amino)-1H-indol-2yl)-carbonyl)-piperazine Table 3: HIV RT wild-type and drug resistance mutation probes. The probes witheld after selection are indicated as "y".

Table 4: Prediction and prevalence of LiPA probe reactivity. Probe names corresponding with the selected motifs are presented in the left column, with the relevant part of each probe shown under the consensus. The prevalence of these motives, determined using panels of European and US sera, is given in the middle column. The right column indicates the corresponding strips of FIGS. 2A–F and the accession number of the reference panel clone used to obtain this reactivity.

EXAMPLES

Example 1 a. Materials and Methods.

Plasma samples were taken from HIV type-1 infected patients and stored at −20° C. until use. Patients were treated with AZT, ddI, ddC, D4T, 3TC, or several combinations of these prodrugs. The European serum samples tested were randomly selected. For the US serum collection, only the first sample from a follow-up series was taken. Some of these US patients were treated, others were not treated.

HIV RNA was prepared using the guanidinium-phenol procedure. Fifty µl plasma was mixed with 150 µl Trizol®LS Reagent (Life Technologies, Gent, Belgium) at room temperature (volume ratio: 1 unit sample/3 units Trizol). Lysis and denaturation occured by carefully pipetting up and down several times, followed by an incubation step at room temperature for at least 5 minutes. Fourty µl CHCl$_3$ was added and the mixture was shaken vigorously by hand for at least 15 seconds, and incubated for 15 minutes at room temperature. The samples were centrifuged at maximum 12,000 g for 15 minutes at 4° C., and the colourless aquous phase was collected and mixed with 100 µl isopropanol. To visualize the minute amounts of viral RNA, 20 µl of 1 µg/µl Dextran T500 (Pharmacia) was added, mixed and left at room temperature for 10 minutes. Following centrifugation at max. 12,000 g for 10 minutes at 4° C. and aspiration of the supernatant, the RNA pellet was washed with 200 µl ethanol, mixed by vortexing and collected by centrifugation at 7,500 g for 5 minutes at 4° C. Finally the RNA pellet was briefly air-dryed and stored at −20° C.

For cDNA synthesis and PCR amplification, the RNA pellet was dissolved in 15 µl random primers (20 ng/µl, pdN$_6$, Pharmacia), prepared in DEPC-treated or HPLC grade water. After denaturation at 70° C. for 10 minutes, 5 µl cDNA mix was added, composed of 4 µl 5×AMV-RT buffer (250 mM Tris.HCl pH 8.5, 100 mM KCl, 30 mM MgCl$_2$, 25 mM DTT), 0.4 µL 25 mM dXTPs, 0.2 µl or 25U Ribonuclease Inhibitor (HPRI, Amersham), and 0.3 µl or 8U AMV-RT (Stratagene). CDNA synthesis occurred during the 90 minutes incubation at 42° C. The HIV RT gene was then amplified using the following reaction mixture. 5 µl cDNA; 4.5 µl 10× Taq buffer, 0.3 µl 25 mM dXTPs, 1 µl (10 pmol) of each PCR primer, 38 µl H$_2$O, and 0.2 µl (1 U) Taq. The primers for amplification had the following sequence: outer sense RT-9: 5' bio-GTACAGTATTAGTAGGACCTA-CACCTGTC 3' (SEQ ID NO 162); nested sense RT-1: 5' bio-CCAAAAGTTAAACAATGGCCATTGACAGA 3' (SEQ ID NO 163); nested antisense RT-4: 5' bio-AGTTCATAACCCATCCAAAG 3' (SEQ ID NO 164); and outer antisense primer RT-12: 5' bio-ATCAGGATGGA-GTTCATAACCCATCCA 3' (SEQ ID NO 39). Annealing occurred at 57° C., extension at 72° C. and denaturation at 94° C. Each step of the cycle took 1 minute, the outer PCR contained 40 cycles, the nested round 35. Nested round PCR products were analysed on agarose gel and only clearly visible amplification products were used in the LiPA procedure. Quantification of viral RNA was obtained with the HIV Monitor™test (Roche, Brussels, Belgium).

Selected PCR products, amplified without 5' biotine primers, were cloned into the pretreated EcoRV site of the pGEMT vector (Promega). Recombinant clones were selected after α-complementation and restriction fragment length analysis, and sequenced with plasmid primers and internal HIV RT primers. Other biotinylated fragments were directly sequenced with a dye-terminator protocol (Applied Biosystems) using the amplification primers. Alternatively, nested PCR was carried out with analogs of the RT-4 and RT-1 primers, in which the biotine group was replaced with the T7- and SP6-primer sequence, respectively. These amplicons were than sequenced with an SP6- and T7-dye-primer procedure. Sequence information was submitted to the GENBANK.

Probes were designed to cover the different polymorphisms and drug induced mutations. In principle, only probes that discriminated between one single nucleotide variation were retained. However, for certain polymorphisms at the extreme ends of the the probe, cross-reactivity was tolerated. Specificity was reached for each probe individually after considering the % (G+C), the probe lenght, the final concentration of the buffer components, and hybridization temperature. Optimized probes were provided enzymatically with a poly-T-tail using the TdT (Pharmacia) in a standard reaction condition, and purified via precipitation. Probe pellets were disolved in standard saline citrate (SSC) buffer and applied as horizontal parallel lines on a membrane strip. Control lines for amplification (probe 5' CCACAGG-GATGGAAAG 3', HIV RT aa 150 to aa 155) and conjugate incubation (biotinylated DNA) were applied alongside. After fixation of the probes onto the membranes by baking, membranes were sliced into 4 mm strips.

To perform LiPA tests, equal amounts (10 μl) of biotinylated amplification products and denaturation mixture (0.4 N NaOH/0.1% SDS) were mixed, followed by an incubation at room temperature for 5 minutes. Following this denaturation step, 2 ml hybridization buffer (2×SSC, 0.1% SDS, 50 mM Tris pH 7.5) was added together with a membrane strip and hybridization was carried out at 39° C. for 30 min. Then, the hybridization mixture was replaced by stringent washing buffer (same composition as hybridisation buffer), and stringent washing occured first at room temperature for 5 minutes and than at 39° C. for another 25 minutes. Buffers were than replaced to be suitable for the streptavidine alkaline phosphatase conjugate incubations. After 30 minutes incubation at room temperature, conjugate was rinsed away and replaced by the substrate components for alkaline phosphatase, Nitro-Blue-Tetrazolium and 5-Bromo-4-Chloro-3-Indolyl Phosphate. After 30 minutes incubation at room temperature, probes where hybridization occured became visible because of the purple brown precipitate at these positions.

b. Results.

b.1 The HIV-1 RT Gene PCR and Selection of a Reference Panel.

PCR primers were chosen outside the target regions for probe design. The amplified region located inside the nested primers covered the HIV-1 RT gene from codon 29 to codon 220. The primer design was based on published sequences from the HIV-1 genotype B clade. European and United States HIV-1 positive serum samples, stored appropriately (at −20° C.) without repeating freezing-thawing cycles, were PCR positive in 96% of the cases (not shown). The annealing temperature for the selected primers seemed to be crucial (57° C.). At 55° C., a second aspecific amplicon of approximately 1500-bp was generated; and at 59° C. the amount of specific fragment decreased drastically. With the current primer combination, the corresponding RT region could be amplified from isolates of the genotype A, C, D and F clade, but with a reduced sensitivity.

A total of 25 selected PCR fragments with the target polymorphisms and mutations were retained as reference panel and sequenced on both strands. The selection occurred during the evaluation of the probes, and these samples originated from naive or drug-treated European or US patients. Biotinylated PCR products from this panel (Accession Number L78133 to L78157) were used to test probes for specificity and sensitivity.

b.2 Nucleotide Target Region for Probe Design and Probe Selection.

Table 4 and parts of FIG. 1 are a compilation of the natural and drug-selected variability in the vicinity of aa 41, 69–70, 74–75, 184, 215, and 219 of the HIV RT gene. To create this table and parts of this figure, the "National Centre for Biotechnology Information" database was searched and all HIV-1 genome entries were retrieved and analyzed one by one. Only those entries displaying non-ambiguous sequence information in the vicinity of the above-mentioned codons were retained for further interpretation. It should be noted that the indicated variations do not imply that they occur in the same sequence: for example the variability observed at codon 40 and 43 may occasionally occur together, but most often, if they occur, only one of them is found. In these 6 regions, a total of 19 different third-letter and two first-letter (codon 43 AAG versus GAG and codon 214 TTT versus CTT) polymorphisms need to be included in the selection of wild type probes. Another 13 first-letter and/or second-letter variations are drug-induced and are the main targets for the selection of probes (FIG. 1).

For the design of relevant probes, only those database motifs that systematically returned (highly prevalent motif) were included, while scattered mutations which were found randomly (low prevalent motif, not shown) were ignored. Based on database sequences, seven motifs for codon 41 (91.6% of all entrees), 6 for codon 69–70 (86.2%), 2 for codon 74–75 (90.4%), 5 for codon I84 (96.6%), 9 for codon 215 (94.1%), and 2 for codon 219 (88.2%) were selected (Table 4).

Probe names corresponding with the selected motifs are presented in the left column of Table 4, with the relevant sequence part of each probe shown under the consensus. The prevalence of these motives was than determined using panels of European and US sera (Table 4).

In many cases, the database entries were not representative for the samples tested. Upon analyzing the European and US samples, many were not reactive with these database-selected probes. Upon sequencing analysis of several of these unreactive PCR products, another 8 motifs became apparent, for which the corresponding probes were designed (41w20, 41m12, 70m13, 74w9, 74m6, 74m12, 184w24, 215m49). By including these newly designed motifs, negative results were markedly decreased; for all codon positions except codon 219, the total percentage of reactivity exceeds 90%.

Another 4 probes were designed (41m11, 215m50, 219m7, and 219m9) because their sequence motif was found in the cloned reference panel, although no reactivity with the tested plasma virus samples was found so far. The existence of these rare sequence motifs is explained by assuming that they exist at an extremely low frequency in the viral quasispecies, remaining undetectable by direct detection methods, but becoming apparent after cloning.

The sequence motif of probe 215m13 was generated in recombinant clones by site-directed mutagenesis (not shown). The rational behind this probe design was to determine whether the sequence combination of codon Y215 (TAC) can occur in combination with L214 (CT) in vivo. However, this latter motif was not found in the plasma samples tested.

Four probes (41w15, 70w8, 215w29, 215w27) are in fact redundant, because they detect identical sequence motifs covered by other probes. However, the location of these redundant probes is slightly different to their sequence-identical counterpart. These probes have the potential to avoid negative results which might otherwise appear as a consequence of random mutations in the probe target area and can therfore increase the specificity of recognition.

b.3 Probe Specificity and Sensitivity.

The 48 selected probes were applied separately on LiPA strips. Biotinylated PCR fragments generated from the reference panel or directly from plasma virus were alkali-denatured, the hybridization buffer and LiPA strips were added, and submitted to stringent hybridization and washing conditions. Positions where hybridization occurred were revealed by the biotine-streptavidine calorimetric detection system. FIGS. 2 (A to F) shows the reactivity of these 48 designed probes. In the right columns of Table 4, there is the indication of the corresponding strip in FIG. 2, and the accession number of the reference panel clone used to obtain this reactivity. The reactivities of these probes were concordant with the nucleotide sequences. False positive reactivities were observed only for probe 41w19 (FIG. 2A.9) and for 70m3 (FIG. 2B.8), with extremely rare sequence motifs 41m12 (prevalence less than 0.3%) and 70m16 (not experimentally found), respectively. Weak cross-reactivity, as was observed on probe 41m13 with a 41m27 motif (FIG. 2A.10) was, in general, not tolerated in the probe design. When occurring, however, it never influenced the genotypic resistance interpretation.

b.4 Applicability of the LiPA in Patient Management.

We selected follow-up samples from three patients and analyzed the viral genotype on the 48 LiPA probes. FIG. 3 illustrates the applicability of genotypic resistance measurement in conjunction with the analysis of viral load and CD4 cell count. All three patients had a wild type virus (i.e. M41-T69-K70-L74-V75-M184-F214-T219-K219) strain in the sample collected before anti-retroviral treatment. Codon positions that changed upon treatment are presented in FIG. 3.

From Patient 91007, 11 serum samples were analyzed, the first sample being collected 2 weeks before the start of therapy. The LiPA revealed that before treatment, in a T215 context, two variants at codon position 213 were predominantly present (GGG and GGA respectively detected by probe 215w11 and 215w9/215w29). From week 50 until week 81, a mixture of T215 and Y215 could be detected. Both variants at codon 213 were also represented in the selected resistant genotypes (probes 215m17 and 215m14 are positive). From week 94 onwards, only Y215 mutant virus could be detected. A nearly identical geno-conversion at codon 41 was observed, with the detection of mixtures (M41 and L41) from week 81 until week 111; from week 126 onwards, only L41 could be found (strips not shown). CD4 values were highly variable. Nevertheless, a continuous decrease in CD4 is apparent (p=0.019, linear regression analysis). Viral load also decreased initially. However, the direct response to the treatment might have been missed in this follow-up series, since the first sample after the start of the treatment is at 32 weeks. From than on, viral load increased.

Patient 94013 was treated with 3TC monotherapy from week 2 onwards. At week 10, a mixture of M184 and V184 could be detected. From week 14 on, only V184 was present. CD4 counts increased nearly 2.5-fold, with the highest level at week 10. Viral load decreased spectacularly by 3 log units. But from week 10 onwards, a slight but steady increase to week 23 was noted. The decrease in CD4 and increase in viral load coincided with the appearance of the V184 motif.

Patient 92021 was followed for 55 weeks. AZT treatment started at week 10, followed by a supplemental ddC treatment from week 20 onwards. The first sample was found to be reactive with probe 215w9/w29 (F214T215=TTTACC), but trace amounts of reactivity with 215w53 (L214T215= TTAACC) could be detected as well, indicating the presence of at least two variants at that time. From week 19 onwards, the codon L214=TTA motif became more important. At week 42, the first sign of genotypic resistance could be detected by the presence of a F214Y215 motif (TTTTAT). Finally at week 55, only F214Y215 could be detected. The L214=TTA motif disappeared completely. At week 42, a mixture (K and R) at codon 70 was present, but at week 55, only R70 could be detected. At week 55, a mixture of codon 219 motifs (K and E) was found (strips not shown). CD4 initially increased, with a maximal effect during AZT monotherapy peaking at week 21. From then on, a continuous decrease was observed. However, ten weeks of AZT treatment did not result in a drop in viral load, since the values of week 16 and 19 were nearly unchanged. It is only after start of the combination therapy (week 20) that the viral load dropped by 1.67 log. From this patient, it is tempting to assume that L214T215 confers genotypic resistance to AZT treatment, and that the addition of ddC is necessary to induce the natural F214Y215 genotype. The rise in CD4 cell count may be the consequence of the drug itself, and not from drug-induced protection (Levy et al. 1996).

c. Discussion

By adapting the previously designed LiPA technology (Stuyver et al. 1993) for the HIV RT gene, the described assay format permits the rapid and simultaneous detection of wild type and drug-selected variants associated with the genotypic resistance for AZT, ddI, ddC, d4T, FTC and 3TC. The Inno LiPA HIV drug-resistance strip provides information about the genetic constitution of the RT gene in the vicinity of codon 41, 69, 70, 74, 75, 184, 215, and 219 at the nucleotide and, hence, also at the deduced protein level. Essentially, the biotinylated RT PCR product is hybridized against immobilized specific oligonucleotides (Table 4), which are directed against the indicated codon variabilities. Following this reverse-hybridization, the oligonucleotide-biotinylated-PCR-strand hybrid is recognized by the streptavidine-alkaline phosphate conjugate, which then in turn converts the alkaline phosphate substrate into a purple brown precipitate.

Using this assay, we studied the specificity and reactivity of 48 probes, covering 6 different regions. This combination should allow the reliable detection of most of the genetic resistance-related codon combinations observed to date. Occasionally occurring mutations in the vicinity of the target codons, not taken into consideration during probe design, may eventually prevent hybridization of the probes for a particular target region. This problem is partially solved by the redundancy of probes at the most important codons. Results obtained using 358 HIV infected plasma samples showed that, depending on the codon position under investigation, between 82.4% and 100% of the combinations could be detected, or an average of 92.7%. It is important to mention here that the assay was developed for resistence detection of the HIV-1 genotype B, and only limited information is currently available about the outcome of this assay with other genotypes. Since the amplification primer combination is more or less universal for all the HIV-1 isolates, some of the indeterminate results may well be due to the presence of non-genotype B virus strains.

So far, several assays for the detection of the wild-type and drug-selected mutations in the HIV RT gene have been described. These include Southern blotting (Richman et al., 1991), primer-specific PCR (Larder et al., 1991), PCR-LDR (Frenkel et al., 1995), RNAse A mismatch cleaving (Galandez-Lopez et al., 1991), and hybridization against enzyme-labeled probes (Eastman et al., 1995). The general advantage of the LiPA and other genotypic assays is the speed by which results are obtained when compared to phenotypic assays. The particular advantage of our test is its multi-parameter (in this particular case multi-codon) format. Moreover, the assay can easily be extended not only for the screening of the other RT-codons, but also for proteinase codons associated with resistance (Mellors et al., 1995). As was illustrated in FIG. 3, mixtures of wild-type and drug-selected mutations can be detected easily. The detection limit for these mixtures is dependent on the sensitivity of the probes, but reliable results can be obtained as soon as 5 to 10% of the minor component is present (not shown). We were unable to provide reliable evidence for mixtures with any sequencing protocol at the same sensitivity level.

Due to the large amount of variables that need to be included in the selection of specific probes (temperature of hybridization, ionic strength of hybridization buffer, length of the probe, G+C content, strand polarity), it might occasionally occur that some of the probes will show weak false positive reaction with related but hitherto unreported sequences. In our experience, and if this occurred, this has never influenced the interpretation at the deduced aa level. In the current selection of probes, all except two (41w19 and 70m3) were retained on the basis of 100% specificity: as soon as one nucleotide differs in the probe area, hybridization is abolished. Further fine-tuning of these two probes will therefore be necessary to obtain the required specificity.

Accompanying polymorphisms in the vicinity of the target codons are found with a rather high prevalence in wild-type virus strains, but not in mutant sequences. A partial list of such combinations is hereby presented: codon V74=GTA without polymorphism at codon 73, 75 or 76; codon V184=GTG without codon Q182=CAG; and codon F215=TTC without F214=TTC/TTA or L214=CTT. The most intriguing example is the following: L214T215 (CTTACC) is predicted for approximately 7.8% of the wild type sequences. The corresponding motif L214Y215 (CTTTAT) apparently does not exist in plasma virus. From the example shown in FIG. 3, it is clear that selection of mutants is a very flexible and complex phenomena. In this particular case, viruses having codon F214 were replaced by a L214 viral population in the AZT monotherapy period, but upon selecting for genotypic drug resistance at codon 215, the original F214 configuration was restored. Clearly, the selection for the Y215 genotype prohibits the presence of a L214 genotype. Since no evidence has yet emerged that L214 confers resistance to anti-retroviral compounds, the appearance of this special mutant during the AZT monotherapy period is difficult to interpret. More research will certainly be necessary to clarify this issue. But if L214 should indeed provide low-level genotypic resistance to AZT treatment, approximately 7.8% of the naive infections will not benefit from initial AZT monotherapy.

Since antiviral treatment can result in a marked extension of life expectancy for HIV infected patients, it is of utmost importance to find the best drug regimen for each individual separately. Therefore, monitoring of the magnitude and duration of the virus load and CD4 cell changes is a prerequisite. However, knowledge concerning the genetic constitution of the virus may also be an important factor in designing optimal treatment schedules. Optimizing therapies making good use of available information (viral load, CD4 cell count, genetic resistance) has remained largely unexploited. If this was partially due to the complexity of screening for all the mutational events, the above-described LiPA technology should remove one key obstacle.

In conclusion, we have described a genotypic assay for the detection of wild type and drug selected codons in the HIV RT gene. The combination of the assay result along with viral load and CD4 cell monitoring should permit better design of patient-dependent optimal treatment schedules.

Example 2

Multi-Drug Resistant (MDR) HIV-1 isolates have been described. These MDR isolates are characterized by having mutations in their genome, compared to the wild type HIV-1 genome, which result in a set of amino acid changes. A key mutation leading to multi-drug resistance was found to be localized in codon 151 of the HIV-1 RT gene. Consequently, and as detecting these MDR isolates is clinically important, we designed probes recognizing wild-type (probe 151w2) and mutant (probes 151m4 and 151m19) HIV-1 isolates. Furthermore, the presence of polymorphisms in the direct vicinity of codon 151 (codon 149) and at codon 151 have been described. Therefore, we also designed two additional probes (probes 151w6 and 151w11) which detect these polymorphisms (FIG. 4 and Table 3).

Treatment with non-nucleoside analogues, such as Nevirapine (Boehringer Ingelheim), selects for several amino acid changes in conserved regions of the HIV-1 RT gene. One of the most important amino acid changes is Y181C, a codon change that confers high level resistance. As the detection of this mutation is also clinically important, we designed probes recognizing the wild-type (181w3 and 181w5) and mutant (181m7) isolates (FIG. 4 and Table 3).

FIG. 4 shows the application of the selected probes for codon 151 and 181. The position of the probes on the strips is indicated on the right side of the strips. LiPA strips were incubated with sequence-confirmed PCR fragments, extracted and amplified from: a wild type HIV-1 isolate (strip 1), a wild type HIV-1 isolate with a polymorphism at codon 151 (strip 2) or codon 149 (strip 3), a multi-drug resistant HIV-1 isolate (strip 4) with no information about codon 181 and a non-nucleoside analogue-treated HIV-1 isolate which remained wild type at codon 151(strip 5).

TABLE 1

| AZT | M41L | ATG to TTG or CTG |
|---|---|---|
|  | D67N | GAG to AAC |
|  | K70R | AAA to AGA |
|  | T215Y | ACC to TAC |
|  | T215F | ACC to TTC |
|  | K219Q | AAA to CAA |
|  | K219E | AAA to GAA |
| ddI | K65R | AAA to AGA |
|  | L74V | TTA to GTA |
|  | V75T | GTA to ACA |
|  | M184V | ATG to GTG |
| ddC | K65R | AAA to AGA |
|  | T69D | ACT to GAT |
|  | L74V | TTA to GTA |
|  | V75T | GTA to ACA |
|  | M184V | ATG to GTG |
|  | Y215C | TTC to TGC |
| d4T | I50T | ATT to ACT |
|  | V75T | GTA to ACA |
| 3TC or FTC | M184V | ATG to GTG or GTA |
|  | M184I | ATG to ATA |
| 1592U89 | K65R | AAA to AGA |
|  | L74V | TTA to GTA |
|  | Y115F | TAT to TTT |
|  | M184V | ATG to GTG |

TABLE 2

| Nevirapine | A98G | GCA to GGA |
|---|---|---|
|  | L100I | TTA to ATA |
|  | K103N | AAA to AAC |
|  | V106A | GTA to GCA |
|  | V108I | GTA to ATA |
|  | Y181C | TAT to TGT |
|  | Y181I | TGT to ATT |
|  | Y188C | TAT to TGT |
|  | G190A | GGA to GCA |

TABLE 2-continued

| | | |
|---|---|---|
| TIBO R82150 | L1991 | TTA to ATA |
| TIBO R82913 | L100I | TTA to ATA |
| | K103N | AAA to AAC |
| | V106A | GTA to GCA |
| | E138K | GAG to AAG |
| | Y181C | TAT to TGT |
| | Y188H | TAT to CAT |
| | Y188L | TAT to TTA |
| L697,593 | K103N | AAA to AAC |
| | Y181C | TAT to TGT |
| L697,661 | A98G | GCA to GGA |
| | L100I | TTA to ATA |
| L697,661 | K101E | AAA to GAA |
| | K103N | AAA to AAC |
| | K103Q | AAA to CAA |
| | V108I | GTA to GCA |
| | V179D | GTT to GAT |
| | V179E | GTT to GAG |
| | Y181C | TAT to TGT |
| BHAP U-90152 | P236L | CCT to CTT |
| BHAP U-87201 | K101E | AAA to GAA |
| | K103N | AAA to AAC |
| | Y181C | TAT to TGT |
| | Y188H | TAT to CAT |
| | E233V | GAA to GTA |
| | P236L | CCT to CTT |
| | K238T | AAA to ACA |
| BHAP U-88204 | L100I | TTA to ATA |
| | V106A | GTA to GCA |
| | Y181C | TAT to TGT |
| | Y181I | TGT to ATT |
| HEPT | Y188C | TAT to TGT |
| E-EBU | Y181C | TAT to TGT |
| E-EBU-dM | Y106A | GTA to GCA |
| E-EPU and | Y181C | TAT to TGT |
| E-EPSeU | Y188C | TAT to TGT |
| a-APA R18893 | Y181C | TAT to TGT |
| S-2720 | G190E | GGA to GAA |
| TSAO BM + 51.0836 | E138K | GAG to AAG |
| | Y181C | TAT to TGT |

TABLE 3

HIV RT wild-type and drug resistance

| Formula | probe | Sequentie oligo | SEQ ID NO | PROBE selection |
|---|---|---|---|---|
| *wild-type probes for position M41* | | | | |
| E40M41K43 | 41w7 | AGAAATGGAAAAGGA | 1 | y |
| E40M41K43 | 41w15 | TGTACAGAAATGGAA | 2 | y |
| M41K43 | 41w16 | AAATGGAAAAGGAAG | 3 | |
| E40M41 | 41w18 | TACAGAGATGGAAA | 4 | |
| E40M41K43 | 41w19 | GTACAGAGATGGAAA | 5 | |
| E40M41K43 | 41w20 | AGAGATGGAAAAGA | 6 | y |
| E40M41K43 | 41w30 | AGAAATGGAGAAGGA | 7 | y |
| E40M41 | 41w31 | ACAGAGATGGAAAA | 8 | |
| E40M41 | 41w32 | GTACAGAGATGGAA | 9 | y |
| E40M41K43 | 41w33 | CAGAGATGGAAAAG | 10 | |
| E40M41K43 | 41w34 | AGAAATGGAAAAGA | 11 | |
| E40M41K43 | 41w35 | GAAATGGAAAAAGA | 12 | |
| E40M41K43 | 41w36 | CAGAAATGGAAAAGA | 13 | y |
| E40M41K43 | 41w37 | AGAAATGGAAAAGAA | 14 | |
| *drug-induced variant probes for position L41* | | | | |
| E40L41K43 | 41m8 | AGAATTGGAAAAGGA | 15 | |
| E40L41K43 | 41m11 | AGAGTTGGAAAAGGA | 16 | y |
| E40L41K43 | 41m12 | AGAGCTGGAAAAGG | 17 | y |
| E40L41K43 | 41m13 | AGAACTGGAAAAGG | 18 | y |
| E40L41K43 | 41m14 | GAGCTGGAAAAGG | 19 | |
| E40L41K43 | 41m21 | ACAGAATTGGAAAAG | 20 | y |
| E40L41 | 41m22 | ACAGAATTGGAAAA | 21 | |

TABLE 3-continued

HIV RT wild-type and drug resistance

| Formula | probe | Sequentie oligo | SEQ ID NO | PROBE selection |
|---|---|---|---|---|
| E40L41 | 41m23 | ACAGAACTGGAAAA | 22 | |
| E40L41K43 | 41m24 | AGAATTGGAAGAGG | 23 | y |
| E40L41E43 | 41m25 | CAGAATTGGAAGAGG | 24 | |
| E40L41E43 | 41m26 | AGAATTGGAAGAGGA | 25 | |
| E40L41E43 | 41m27 | AGAACTGGAAGAGG | 26 | y |
| E40L41E43 | 41m28 | CAGAACTGGAAGAGG | 27 | |
| E40L41E43 | 41m29 | AGAACTGGAAGAGGA | 28 | |
| *wild-type probes for positions I50 or V50 or T50* | | | | |
| K49I50 | 50w4 | CAAAAATTGGGCCT | 29 | y |
| R49I50 | 50w9 | ATTTCAAGAATTGGG | 30 | y |
| K49V50 | 50w5 | TTCAAAAGTTGGGC | 31 | y |
| K49I50 | 50w13 | CAAAAATCGGGCCTG | 32 | y |
| K49T50 | 50w14 | AAAAATCGGGCCTGA | 33 | y |
| *wild-type probe for position D67* | | | | |
| K64K65K66D67 | 67w4 | AAAGAAGAAAGACAG | 34 | y |
| *drug-induced variant probe for position N67* | | | | |
| K64K65K66N67 | 67m19 | ATAAAGAAAAAGAACAGTA | 35 | y |
| *wild-type probes for positions T69 or K70* | | | | |
| T69K70 | 70w1 | AGTACTAAATGGAGAA | 36 | y |
| D69K70 | 70w2 | AGTGATAAATGGAGAA | 37 | y |
| T69K70 | 70w8 | ACAGTACTAAATGGAG | 38 | y |
| K70K73 | 70w11 | TAAATGGAGAAAAITAG | 40 | |
| *drug-induced variant probes for positions D69 or N69 or A69 or R70* | | | | |
| D69R70 | 70m3 | GTGATAGATGGAGAA | 41 | |
| T69R70 | 70m6 | GTACTAGATGGAGA | 42 | |
| T69R70 | 70m12 | AGTACTAGATGGAGA | 43 | y |
| T69R70 | 70m13 | AGTACAAGATGGAGA | 44 | y |
| N69R70 | 70m14 | CAGTAATAGATGGAG | 45 | y |
| A69R70 | 70m15 | ACAGTGCTAGATGGA | 46 | |
| A69R70 | 70m16 | CAGTGCTAGATGGA | 47 | y |
| A69R70 | 70m17 | CAGTGCTAGATGGA | 48 | |
| D69R70 | 70m18 | CAGTGATAGATGGA | 49 | y |
| D69R70 | 70m19 | CAGTGATAGATGGAG | 50 | |
| D69R70 | 70m20 | AGTGATAGATGGAG | 51 | |
| D69R70 | 70m21 | AGTGATAGATGGAGA | 52 | |
| *wild-type probes for positions L74 or V75* | | | | |
| K73L74V75D76 | 74w5 | GAGAAAATTAGTAGATTT | 53 | y |
| K73L74V75D76 | 74w8 | AAAATTAGTAGACTTC | 54 | y |
| K73L74V75D76 | 74w9 | GAGAAAGTTAGTGGATT | 55 | |
| *drug-induced variant probes for positions V74 or T75* | | | | |
| K73V74V75D76 | 74m6 | AGAAAAGTAGTAGATTT | 56 | y |
| K73L74T75D76 | 74m10 | AAAATTAACAGATTTC | 57 | |
| K73L74T75D76 | 74m11 | GAAAATTAACAGATTT | 58 | |
| K73L74T75D76 | 74m12 | GAAAATTAACAGATTTC | 59 | y |
| *wild-type probes for position Q151* | | | | |
| P150Q151G152 | 151w2 | CTTCCACAGGGATGG | 60 | y |
| P150Q151G152 | 151w6 | CTTCCACAAGGATGG | 61 | y |
| P150Q151G152 | 151w11 | TGCTCCCACAGGGATG | 62 | y |
| *drug-induced variant probe for position M151* | | | | |
| P150M151G152 | 151m4 | CTTCCAATGGGATGG | 63 | y |
| P150M151G152 | 151m19 | GCTTCCAATGGGATGG | 64 | y |
| *wild-type probe for position Y181* | | | | |
| Y181 | 181w3 | AGTTATCTATCAATACAG | 65 | y |

TABLE 3-continued

HIV RT wild-type and drug resistance

| Formula | probe | Sequentie oligo | SEQ ID NO | PROBE selection |
|---|---|---|---|---|
| drug-induced variant probe for position C181 | | | | |
| C181 | 181m7 | AGTTATCTGTCAATAC | 66 | y |
| wild-type probes for position M184 | | | | |
| Q182M184 | 184w11 | TCAATACATGGATGAGG | 67 | y |
| Q182M184 | 184w17 | TCAGTACATGGATGAGG | 68 | y |
| Q182M184 | 184w18 | ATCAATACATGGATGA | 69 | |
| Q182M184 | 184w19 | TCAGTACATGGATG | 70 | |
| Q182M184 | 184w21 | ATCAATATATGGATG | 71 | y |
| Q182M184 | 184w22 | ATCAATATATGGATGA | 72 | |
| Q182M184 | 184w23 | TCAATATATGGATGA | 73 | |
| Q182M184 | 184w24 | TCAATACATGGACGA | 74 | y |
| Q182M184 | 184w25 | CAATACATGGACGAT | 75 | |
| Q182M184 | 184w26 | TCAATACATGGACGAT | 76 | |
| drug-induced variant probes for position V184 or I184 | | | | |
| Q182V184 | 184m12 | CAATACGTGGATGAGGG | 77 | y |
| I184 | 184m13 | AATACATAGATGAT | 78 | |
| Q182I184 | 184m14 | CAATACATAGATGAT | 79 | |
| Q182I184 | 184m15 | CAATACATAGATGATT | 80 | |
| Q182V184 | 184m16 | CAATACGTAGATGAT | 81 | |
| Q182V184 | 184m20 | TCAATACGTGGATGA | 82 | |
| Q182I184 | 184m27 | TCAATACATAGATGAT | 83 | |
| Q182I184 | 184m28 | ATCAATACATAGATGAT | 84 | y |
| wild-type probes for position T215 | | | | |
| G213F214T215 | 215w9 | GGATTTACCACACCA | 85 | y |
| L214T215 | 215w10 | GACTTACCACACCA | 86 | y |
| F214T215 | 215w11 | GGTTTACCACACCA | 87 | y |
| F214T215 | 215w16 | GATTTACCACACCA | 88 | |
| T215 | 215w22 | TTACTACACCAGAC | 89 | y |
| T215 | 215w24 | TTACCACACCAGA | 90 | |
| G213L214T215 | 215w27 | TGGGGACTTACCAC | 91 | y |
| G213F214T215 | 215w29 | TGGGGATTTACCAC | 92 | y |
| G213F214T215 | 215w32 | GGGGTTCACCACAC | 93 | |
| G213F214T215 | 215w33 | GGGATTCACCACAC | 94 | y |
| G213F214T215 | 215w34 | GGGATTTACCACACCAG | 95 | |
| G213L214T215 | 215w35 | TGGGGACTTACCACACC | 96 | |
| G213F214T215 | 215w36 | TGGGGGTTTACCACACC | 97 | |
| G213F214T215 | 215w37 | GGGATTTACTACACCAG | 98 | |
| G213L214T215 | 215w52 | GGGATTAACCACAC | 99 | |
| G213L214T215 | 215w53 | GGGGATTAACCACA | 100 | y |
| G213L214T215 | 215w54 | TGGGGATTAACCACA | 101 | |
| G213L214T215 | 215w55 | GGGGGTTAACCACA | 102 | |
| G213L214T215 | 215w56 | GGGGTTAACCACAC | 103 | |
| G213L214T215 | 215w57 | TGGGGGTTAACCAC | 104 | |
| G213L214T215 | 215w65 | GGGATTGACCACAC | 105 | |
| G213L214T215 | 215w66 | GGATTGACCACACC | 106 | |
| G213L214T215 | 215w67 | GGGATTGACCACA | 107 | y |
| G213L214T215 | 215w68 | GGGACTGACCACA | 108 | y |
| G213L214T215 | 215w69 | GGGACTGACCACAC | 109 | |
| G213L214T215 | 215w70 | TGGGGGTTAACCACA | 110 | |
| G213L214T215 | 215w71 | TGTGGTTAACCCCCA | 111 | y |
| G213L214T215 | 215w51 | GGGGCTTACCACAC | 112 | |
| drug-induced variant probes for position Y215 or F215 | | | | |
| G213L214Y215 | 215m13 | GGACTTTACACACC | 113 | y |
| G213F214Y215 | 215m14 | GGGTTTTACACACC | 114 | y |
| G213F214F215 | 215m15 | GGATTTTTCACACCA | 115 | |
| G213F214Y215 | 215m17 | GGATTTTACACACC | 116 | y |
| G213F214F215 | 215m38 | GGGATTTACACACCAG | 117 | |
| G213F214F215 | 215m39 | GGGATTTTTCACACCAG | 118 | |
| G213F214Y215 | 215m40 | GGGATTTACACAC | 119 | |
| G213F214Y215 | 215m41 | GGGGATTTTACACA | 120 | |
| G213F214Y215 | 215m43 | CCCTAAAATGTGTG | 121 | |
| G213F214F215 | 215m44 | GGATTTTTCACACC | 122 | |
| F214F215 | 215m45 | GATTTTTCACACCA | 123 | y |
| G213F214F215 | 215m46 | GGGATTTTTCACAC | 124 | |
| G213F214Y215 | 215m42 | CCCCTAAAATGTGT | 125 | |
| F214Y215 | 215m47 | GGTTTTATACACCA | 126 | |
| G213F214Y215 | 215m48 | GGGTTTTATACACC | 127 | |
| G213F214Y215 | 215m49 | GGGGTTTTATACAC | 128 | y |
| G213L214T215 | 215m50 | GGGGGCTTACCACA | 129 | y |
| G213F214Y215 | 215m61 | GGATTCTACACACC | 130 | y |
| F214Y215 | 215m62 | GATTCTACACACC | 131 | |
| G213F214Y215 | 215m63 | GGATTCTACACAC | 132 | |
| G213F214Y215 | 215m64 | GGGATTCTACACAC | 133 | |
| G213F214Y215 | 215m72 | GGGTTTTATACCCC | 134 | |
| F214Y215 | 215m73 | GGTTTTATACCCC | 135 | |
| F214Y215 | 215m74 | GTTTTATACCCCA | 136 | |
| wild-type probes for position K219 | | | | |
| K219 | 219w1 | ACCAGACAAAAACA | 137 | |
| K219 | 219w2 | ACCAGACAAAAAC | 138 | y |
| K219 | 219w3 | CACCAGACAAAAAAC | 139 | |
| K219 | 219w13 | CAGACAAGAAACAT | 140 | |
| K219 | 219w14 | CCAGACAAGAAACA | 141 | |
| K219 | 219w15 | ACCAGACAAGAAACA | 142 | |
| K219 | 219w16 | AGACAAAAAGCATC | 143 | y |
| K219 | 219w17 | CAGACAAAAAGCAT | 144 | |
| K219 | 219w18 | CAGACAAAAAGCATC | 145 | |
| K219 | 219w19 | CCAGATAAAAACA | 146 | |
| K219 | 219w20 | ACCAGATAAAAAC | 147 | |
| K219 | 219w21 | CCCAGATAAAAACA | 148 | |
| K219 | 219w22 | CCAGATAAAAACATC | 149 | |
| K219 | 219w23 | CACCAGATAAAAAC | 150 | |
| K219 | 219w24 | CAGACAAGAAACATC | 151 | |
| K219 | 219w25 | ACCAGACAAGAAAC | 152 | |
| drug-induced variant probes for position Q219 or E219 | | | | |
| Q219 | 219m4 | ACCAGACCAAAAACA | 153 | |
| E219 | 219m5 | ACCAGACGAAAAACA | 154 | |
| Q219 | 219m6 | ACCAGATCAAAAACA | 155 | |
| Q219 | 219m7 | ACCAGATCAAAAAC | 156 | y |
| Q219 | 219m8 | CACCAGATCAAAAAC | 157 | |
| E219 | 219m9 | ACCAGACGAAAAAC | 158 | y |
| E219 | 219m10 | CCAGACGAAAAACA | 159 | |
| Q219 | 219m11 | CCAGACCAAAAACA | 160 | |
| Q219 | 219m12 | ACCAGACCAAAAAC | 161 | |

TABLE 4

Prediction and prevalence of LiPA probe reactivity

| probe | consensus nucleic acid | amino acid | prevalence database | Europe | US | Rp | Corresponding Figure strip | Acc. Nb |
|---|---|---|---|---|---|---|---|---|
| probe | Codon 38–43 | | n = 191/m = 25 | n = 306 | n = 52 | n = 25 | | |
| | TGTACAGAAATGGAAAAG | CTEMEK | | | | | | |
| 41w7 | ---------------- | ------ | 122 (62.9%) | 237 | 35 | 11 | 1a.1 | L78149 |
| 41w15* | ---------------- | ------ | 118 | 230 | 38 | 9 | 1a.1 | L78149 |
| 41w19 | -----G---------- | ------ | 5 (2.6%) | 10 | 2 | 2 | 1a.2 | L78156 |
| 41w20 | --G--------A---- | ------ | 0 | 6 | 0 | 1 | 1a.3 | L78157 |
| 41w30 | --------G------- | ------ | 1 (0.5%) | 8 | 6 | 1 | 1a.4 | L78154 |
| 41m21 | ------T--------- | --L-- | 18 (9.4%) | 37 | 7 | 2 | 1a.5 | L78136 |
| 41m11 | --GT------------ | -L-- | 0 | 0 | 0 | 1 | 1a.6 | L78140 |
| 41m24 | ---T-----G------ | -L-E | 12 (6.3%) | 1 | 2 | 1 | 1a.7 | L78144 |
| 41m13 | ---C------------ | -L-- | 14 (7.3%) | 21 | 3 | 1 | 1a.8 | L78139 |
| 41m12 | --GC------------ | -L-- | 0 | 1 | 0 | 1 | 1a.9 | L78155 |
| 41m27 | ---C-----G------ | -L-E | 3 (1.6%) | 0 | 1 | 1 | 1a.10 | L78137 |
| | | total | 175 (91.6%) | 95.1% | 100% | 88% | | |
| probe | Codon 68–72 | | n = 354/m = 32 | n = 306 | n = 52 | n = 25 | | |
| | AGTACTAAATGGAGA | STKWR | | | | | | |
| 70w1 | --------------- | ----- | 224 (63.3%) | 230 | 39 | 13 | 1b.1,2 | L78147 |
| 70w8* | --------------- | ----- | 208 | 210 | 38 | 11 | 1b.2 | L78144 |
| 70m12 | -------G------- | --R-- | 37 (10.5%) | 46 | 6 | 4 | 1b.3 | L78148 |
| 70m13 | -----A-G------- | --R-- | 0 | 0 | 1 | 2 | 1b.4 | L78133 |
| 70w2 | ---GA---------- | -D--- | 25 (7.1%) | 4 | 4 | 2 | 1b.5 | L78136 |
| 70m3 | GA--G---------- | DR-- | 10 (2.8%) | 3 | 1 | 0 | 1b.6 | pending |
| 70m14 | --------------- | -NR- | 7 (2.0%) | 4 | 5 | 2 | 1b.7 | L78154 |
| 70m16 | ---G---G------- | -AR- | 2 (0.6%) | 0 | 0 | 1 | 1b.8 | L78150 |
| | | total | 305 (86.2%) | 91.8% | 94.2% | 96% | | |
| probe | Codon 72–77 | | n = 364/m = 20 | n = 306 | n = 52 | n = 25 | | |
| | AGAAAATTAGTAGATTTC | RKLVDF | | | | | | |
| 74w5 | ------------------ | ------ | 320 (87.9%) | 264 | 48 | 16 | 1c.1 | L78150 |
| 74w8 | -----------C---- | ------ | 9 (2.5%) | 34 | 1 | 2 | 1c.2 | L78147 |
| 74w9 | -----G------G--- | ------ | 0 | 17 | 3 | 2 | 1c.3 | L78137 |
| 74m6 | ------G--------- | --V-- | 0 | 5 | 0 | 3 | 1c.4 | L78149 |
| 74m12 | ------AC-------- | --T-- | 0 | 1 | 1 | 1 | 1c.5 | L78136 |
| | | total | 329 (90.4%) | 93.5% | 98.1% | 96% | | |
| probe | Codon 182–185 | | n = 322/m = 12 | n = 306 | n = 52 | n = 25 | | |
| | CAATACATGGAT | QYMD | | | | | | |
| 184w11 | ------------ | ---- | 285 (88.5%) | 267 | 46 | 18 | 1d.1 | L78147 |
| 184w17 | --G--------- | ---- | 16 (5.0%) | 9 | 4 | 3 | 1d.2 | L78137 |
| 184w21 | -----T------ | ---- | 6 (1.9%) | 4 | 2 | 1 | 1d.3 | L78145 |
| 184w24 | -----------C | ---- | 0 | 1 | 0 | 1 | 1d.4 | L78144 |
| 184m12 | ------G----- | --V- | 1 (0.3%) | 8 | 0 | 1 | 1d.5 | L78142 |
| 184m28 | --------A--- | --T- | 3 (0.9%) | 0 | 0 | 1 | 1d.6 | L78148 |
| | | total | 311 (96.6%) | 93.8 | 98.1% | 100% | | |
| probe | Codon 212–218 | | n = 321/m = 36 | n = 306 | n = 52 | n = 25 | | |
| | TGGGGATTTACCACACCAGAC | WGFTTPD | | | | | | |
| 215w11 | G-------------- | ---- | 9 (2.8%) | 15 | 3 | 2 | 1e.1 | L78146 |
| 215w9 | ---------------- | ----- | 142 (44.2%) | 178 | 24 | 3 | 1e.2 | L78141 |
| 215w29 f | ------------ | ---- | 142 | 105 | 16 | 3 | 1e.2 | L78141 |
| 215w33 | -----C-------- | ---- | 9 (2.8%) | 8 | 4 | 1 | 1e.3 | L78154 |
| 215w10 | C------------- | L--- | 25 (7.8%) | 10 | 0 | 2 | 1e.4 | L78150 |
| 215w27 f | ------C------- | --L- | 25 | 14 | 0 | 2 | 1e.4 | L78150 |
| 215m50 | --GC---------- | -L-- | 0 | 0 | 0 | 1 | 1e.5 | L78145 |
| 215w53 | -----A-------- | -L-- | 1 (0.3%) | 1 | 3 | 1 | 1e.6 | L78138 |
| 215w22 | --T----------- | ---- | 3 (0.9%) | 10 | 2 | 1 | 1e.7 | L78134 |
| 215m17 | ------TA------ | --Y- | 88 (27.4%) | 50 | 12 | 7 | 1e.8 | L78144 |
| 215m14 | --G---TA------ | --Y- | 24 (7.5%) | 24 | 1 | 1 | 1e.9 | L78149 |

TABLE 4-continued

Prediction and prevalence of LiPA prohe reactivity

| | consensus | | prevalence | | | | Corresponding | |
|---|---|---|---|---|---|---|---|---|
| | nucleic acid | amino acid | database | Europe | US | Rp | Figure | |
| 215m49 | --G---TAT--- | --Y- | 0 | 2 | 0 | 2 | 1e.10 | L78148 |
| 215m45 | ---TT------ | -F-- | 1 (0.3%) | 16 | 0 | 1 | 1e.11 | L78135 |
| 215m13 | ---C--TA---- | -LY-- | 0 | 0 | 0 | 2 | 1e.12 | L78155 |
| | | total | 302 (94.1%) | 92.8% | 90.4% | 96% | | |
| probe | Codon 217–220 | | n = 204/m = 12 | n = 34 | n = 52 | n = 26 | | |
| | CCAGACAAAAAA | PDKK | | | | | | |
| 219w2 | ------------ | ---- | 179 (87.7%) | 26 | 42 | 18 | 1f.1 | L78144 |
| 219m4 | ------C----- | --Q- | 1 (0.5%) | 2 | 4 | 2 | 1f.2 | L78135 |
| 219m7 | -----TC----- | --Q- | 0 | 0 | 0 | 1 | 1f.3 | L78133 |
| 219m9 | ------G----- | --E- | 0 | 0 | 0 | 1 | 1f.4 | pending |
| | | total | 179 (88.2%) | 82.4% | 82.7% | 84.6% | | | n = amount of sequences (database retrieved), or isolates tested
m = amount of motifs corresponding with the n database sequences
*: redundant probes
RP reference panel
The total percentage for European and US samples is not the sum of probe reactivities, but a result of the complete interpretations for these codons.

REFERENCES

Asseline U, Delarue M, Lancelot G, Toulme F, Thuong N (1984) Nucleic acid-binding molecules with high affinity and base sequence specificity: intercalating agents covalently linked to oligodeoxynucleotides. Proc. Natl. Acad. Sci. USA 81(11):3297–301.

Barany F. Genetic disease detection and DNA amplification using cloned thermostable ligase. Proc Natl Acad Sci USA 1991; 88: 189–193.

Bej A, Mahbubani M, Miller R, Di Cesare J, Haff L, Atlas R. Mutiplex PCR amplification and immobilized capture probes for detection of bacterial pathogens and indicators in water. Mol Cell Probes 1990; 4:353–365.

Boom R., Sol C. J. A., Salimans M. M. M., et al. Rapid and simple method for purification of nucleic acids. J Clin Microbiol 1990; 28: 495–503.

Compton J. Nucleic acid sequence-based amplification. Nature 1991; 350: 91–92.

Duck P. Probe amplifier system based on chimeric cycling oligonucleotides. Biotechniques 1990; 9: 142–147.

Eastman S, Boyer E, Mole L, Kolberg J, Urdea M, Holodniy M. Nonisotypic hybridisation assay for determination of relative amounts of genotypic human immunodeficiency virus type 1 zidovudine resistance. 1995; 33: 2777–2780.

Frenkel L. Wagner L. Atwood S, Cummins T, Dewhurst S. Specific, sensitive and rapid assay for human immunodeficiency virus type 1 pol mutations asssociated with resistance to zidovudine and didanosine. J. Clin. Microbiology 1995; 33: 342–347.

Guatelli J. Whitfield K, Kwoh D, Barringer K, Richman D, Gengeras T. Isothermal, in vitro amplification of nucleic acids by a multienzyme reaction modeled after retroviral replication. Proc Natl Acad Sci USA 1990; 87: 1874–1878.

Iversen A. K. N., R. W. Shafer, K. Wehrly, M. A. Winters, J. I. Mullins, B. Chesebro, and T. Merigan. Multidrug-resistant human immunodeficiency virus type 1 strains resulting from combination antiretroviral therapy. J. Virol. 1996; 70:1086–1090.

Kwoh D, Davis G, Whitfield K, Chappelle H, Dimichele L, Gineras T. Transcription-based amplification system and detection of amplified human immunodeficiency virus type 1 with a bead-based sandwich hybridization format. Proc Natl Acad Sci USA 1989; 86: 1173–1177.

Kwok S, Kellogg D, McKinney N, Spasic D, Goda L, Levenson C, Sinisky J. Effects of primer-template mismatches on the polymerase chain reaction: Human immunodeficiency views type 1 model studies. Nucl. Acids Res. 1990; 18: 999.

Landgren U, Kaiser R, Sanders J, Hood L. A ligase-mediated gene detection technique. Science 1988; 241:1077–1080.

Larder B, Kellam P, Kemp S. Zidovudine resistance predicted by direct detecion of mutations in DNA from HIV-infected lymphocytes. Aids 1991; 5: 137–144.

Lomeli H, Tyagi S, Printchard C, Lisardi P, Kramer F. Quantitative assays based on the use of replicatable hybridization probes. Clin Chem 1989; 35: 1826–1831.

Matsukura M, Shinozuka K, Zon G, Mitsuya H, Reitz M, Cohen J, Broder S (1987) Phosphorothioate analogs of oligodeoxynucleotides: inhibitors of replication and cytopathic effects of human immunodeficiency virus. Proc. Natl. Acad. Sci. USA 84(21):7706–10.

Mellors J, Larder B, Schinazzi R. Mutations in HIV-1 reverse transcripatse and protease associated with drug resistance. International Antiviral News (1195); 3: 8–13.

Miller P, Yano J, Yano E, Carroll C Jayaram K, Ts'o P (1979) Nonionic nucleic acid analogues. Synthesis and characterization of dideoxyribonucleoside methylphosphonates. Biochemistry 18(23):5134–43.

Nielsen P, Egholm M, Berg R, Buchardt O (1991) Sequence-selective recognition of DNA by strand displacement with a thymine-substituted polyamide. Science 254 (5037): 1497–500.

Nielsen P, Egholm M, Berg R, Buchardt O (1993) Sequence specific inhibition of DNA restriction enzyme cleavage by PNA. Nucleic-Acids-Res. 21(2) 197–200.

Saiki R, Walsh P, Levenson C, Erlich H. Genetic analysis of amplified DNA with immobilized sequence-specific oligonucleotide probes Proc Natl Acad Sci USA 1989; 86:6230–6234.

Schinazi R, Larder B, Mellors J. Mutations in HIV-1 reverse transcriptase and protease associated with drug resistance. International Antiviral News, 2:72–74.

Stuyver L, Rossau R, Wyseur A, et al. Typing of hepatitis C virus isolates and characterization of new subtypes using a line probe assay. J. Gen. Virol. 1993; 74: 1093–1102.

Wu D, Wallace B. The ligation amplification reaction (LAR)—amplification of specific DNA sequences using sequential rounds of template-dependent ligation. Genomics 1989; 4:560–569.

What is claimed is:

1. A kit for inferring the nucleotide sequence at codons of interest in the HIV reverse transciptase (RT) and/or the amino acids corresponding to these codons and/or the HIV RT resistance spectrum of HIV isolates present in a biological sample comprising:

(i) optionally, a means for releasing, isolating, or concentrating the polynucleic acids present in said sample;

(ii) optionally, at least one suitable set of primers;

(iii) at least two different probes, wherein each probe is capable of hybridizing specifically to one or more target codons within any region I to VIII as represented in FIG. 1, said probes optionally fixed to a solid support;

(iv) a hybridization buffer, or components necessary for producing said buffer;

(v) a wash solution, or components necessary for producing said solution;

(vi) optionally, a means for detecting the hybrids resulting from the preceding hybridization;

(vii) optionally, a means for attaching said probe to a solid support wherein the set of primers is selected from the group consisting of:
SEQ ID No: 162 and 163, and
SEQ ID No: 164 and 39.

2. A kit for inferring the nucleotide sequence at codons of interest in the HIV RT gene and/or the amino acids corresponding to these codons and/or the antiviral drug resistance spectrum of HIV isolates present in a biological sample, the kit comprising the following components:

at least two different probes, wherein the probes are selected from the group consisting of SEQ ID NO: 4, 5, 6, 7, 8, 9, 10, 11, 12, 13, 14, 15, 16, 17, 18, 19, 20, 21, 22, 23, 24, 25, 26, 27, 28, 30, 31, 32, 33, 34, 35, 37, 40, 41, 44, 45, 46, 47, 48, 49, 50, 51, 52, 54, 55, 56, 57, 58, 59, 61, 62, 63, 64, 65, 66, 67, 68, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 114, 115, 117, 118, 119, 120, 121, 122, 124, 125, 126, 127, 128, 129, 130, 131, 132, 133, 134, 135, 136, 138, 140, 141, 142, 143, 144, 145, 146, 147, 148, 149, 150, 151, 152, 154, 155, 156, 157 and 159;

a hybridization buffer, or components necessary for producing said buffer; and a wash solution, or components necessary for producing said solution.

3. The kit according to claim 2 wherein the probes are selected from the group consisting of SEQ ID NO: 4, 8, 9, 10, 11, 12, 13, 14, 15, 19, 21, 22, 24, 25, 27, 28, 30, 31, 32, 33, 34, 35, 40, 46, 48, 49, 50, 51, 52, 54, 55, 56, 57, 58, 70, 72, 73, 75, 76, 78, 79, 80, 81, 82, 83, 86, 88, 90, 93, 95, 96, 97, 98, 99, 101, 102, 103, 104, 105, 106, 107, 108, 109, 110, 111, 112, 115, 117, 118, 119, 120, 121, 122, 124, 125, 126, 127, 128, 129, 130, 131, 132, 133, 134, 135, 136, 138, 140, 141, 142, 143, 144, 145, 146, 147, 148, 149, 150, 151, 152, 154, 155, 157 and 159.

4. The kit according to claim 2 wherein at least one of the probes is selected from the group consisting of SEQ ID NO: 4, 8, 9, 10, 11, 12, 13, 14, 15, 19, 21, 22, 24, 25, 27 and 28.

5. The kit according to claim 2 wherein at least one of the probes is selected from the group consisting of SEQ ID NO: 30, 31, 32, and 33.

6. The kit according to claim 2 wherein at least one of the probes is selected from the group consisting of SEQ ID NO: 34, 35, 40, 46, 48, 49, 50, 51 and 52.

7. The kit according to claim 2 wherein at least one of the probes is selected from the group consisting of SEQ ID NO: 57 and 58.

8. The kit according to claim 2 wherein at least one of the probes is selected from the group consisting of SEQ ID NO: 70, 72, 73, 75, 76, 78, 79, 80, 81, 82 and 83.

9. The kit according to claim 2 wherein at least one of the probes is selected from the group consisting of SEQ ID NO: 86, 88, 90, 93, 95, 96, 97, 98, 99, 101, 102, 103, 104, 105, 106, 107, 108, 109, 110, 111, 112, 115, 117, 118, 119, 120, 121, 122, 124, 125, 126, 127, 128, 130, 131, 132, 133, 134, 135 and 136.

10. The kit according to claim 2 wherein at least one of the probes is selected from the group consisting of SEQ ID NO: 138, 140, 141, 142, 143, 144, 145, 146, 147, 148, 149, 150, 151, 152, 154, 155, 157 and 159.

11. The kit according to claim 2 wherein at least one of the probes is selected from the group consisting of SEQ ID NO: 5, 6, 7, 16, 17, 18, 20, 23, 26, 37, 41, 44, 45, 47, 54, 55, 56, 59, 61, 62, 63, 64, 65, 66, 67, 68, 71, 74, 77, 84, 85, 87, 89, 91, 92, 94, 100, 114, 128, 129, 138 and 156.

12. The kit according to claim 2 wherein at least one of the probes is selected from the group consisting of SEQ ID NO: 5, 6, 7, 16, 17, 18, 20, 23 and 26.

13. The kit according to claim 2 wherein at least one of the probes is selected from the group consisting of SEQ ID NO: 37, 41, 44, 45 and 47.

14. The kit according to claim 2 wherein at least one of the probes is selected from the group consisting of SEQ ID NO: 54, 55, 56 and 59.

15. The kit according to claim 2 wherein at least one of the probes is selected from the group consisting of SEQ ID NO: 61, 62, 63 and 64.

16. The kit according to claim 2 wherein at least one of the probes is selected from the group consisting of SEQ ID NO: 65, 66, 67, 68, 71, 74, 77 and 84.

17. The kit according to claim 2 wherein at least one of the probes is selected from the group consisting of SEQ ID NO: 85, 87, 89, 91, 92, 94, 100, 114, 128 and 129.

18. The kit according to claim 2 wherein at least one of the probes is selected from the group consisting of SEQ ID NO: 138 and 156.

19. The kit of claim 2, further comprising a means for releasing, isolating, or concentrating polynucleic acids present in the sample.

20. The kit of claim 2, further comprising at least one suitable set of primers.

21. The kit according to claim 20, wherein the set of primers is selected from the group consisting of SEQ ID No: 162 and 163, and SEQ ID No: 164 and 39.

22. The kit of claim 2, wherein at least two probes are fixed to a solid support.

23. The kit of claim 2, further comprising a means for detecting hybrids resulting from hybridization of at least one of the two probes to the sample.

* * * * *